United States Patent
Wang et al.

(10) Patent No.: US 8,637,681 B2
(45) Date of Patent: Jan. 28, 2014

(54) PYRROLYL SUBSTITUTED DIHYDROINDOL-2-ONE DERIVATIVES, PREPARATION METHODS AND USES THEREOF

(75) Inventors: Jingyi Wang, Jinan (CN); Chuanwen Fan, Jinan (CN); Long Zhang, Jinan (CN); Boyan Xu, Jinan (CN); Shousheng Yan, Jinan (CN); Zongru Guo, Jinan (CN); Minghui Zhang, Jinan (CN); Dong Lin, Jinan (CN); Zhantao Zhang, Jinan (CN); Haojie Zhou, Jinan (CN)

(73) Assignee: Qilu Pharmaceutical Co., Ltd., Jinan, Shandong (CN)

( * ) Notice: Subject to any disclaimer, the term of this patent is extended or adjusted under 35 U.S.C. 154(b) by 0 days.

(21) Appl. No.: 13/702,956

(22) PCT Filed: Mar. 31, 2011

(86) PCT No.: PCT/CN2011/000561
§ 371 (c)(1),
(2), (4) Date: Feb. 25, 2013

(87) PCT Pub. No.: WO2011/153814
PCT Pub. Date: Dec. 15, 2011

(65) Prior Publication Data
US 2013/0158030 A1 Jun. 20, 2013

(30) Foreign Application Priority Data
Jun. 8, 2010 (CN) .......................... 2010 1 0194609

(51) Int. Cl.
| C07D 401/14 | (2006.01) |
| C07D 403/14 | (2006.01) |
| C07D 413/14 | (2006.01) |
| C07D 411/06 | (2006.01) |
| A61K 31/403 | (2006.01) |
| A61K 31/497 | (2006.01) |
| A61K 31/535 | (2006.01) |

(52) U.S. Cl.
USPC ........... 548/468; 546/201; 544/144; 544/373; 514/235.2; 514/414; 514/254.09; 514/232

(58) Field of Classification Search
None
See application file for complete search history.

(56) References Cited

U.S. PATENT DOCUMENTS
2003/0069297 A1   4/2003  Cui et al.

FOREIGN PATENT DOCUMENTS
WO   2007/085205 A1   8/2007

OTHER PUBLICATIONS

Xiao et al., "Synthesis and Antitumor Evaluation of 3-Substituted Indolin-2-ones," Chinese Journal of Organic Chemistry 29(3): 459-461, 2009.

*Primary Examiner* — Nyeemah A Grazier
(74) *Attorney, Agent, or Firm* — Seed IP Law Group PLLC

(57) ABSTRACT

Provided are pyrrolyl substituted dihydroindol-2-one derivatives represented by formula (I), pharmaceutically acceptable salts or solvates of said derivatives, or solvates of said salts, which are effective tyrosine kinase inhibitors. Also provided are the preparation methods of the above compounds, pharmaceutical compositions containing these compounds, and the use of these compounds in manufacturing drugs useful for the treatment or adjunctive treatment of tumors medicated by tyrosine kinases or proliferation or migration of tumor cells driven by tyrosine kinases in mammals (including human).

8 Claims, No Drawings

PYRROLYL SUBSTITUTED DIHYDROINDOL-2-ONE DERIVATIVES, PREPARATION METHODS AND USES THEREOF

TECHNICAL FIELD

The present invention belongs to the field of pharmaceutical and chemical industry, and relates to pyrrolyl substituted dihydroindol-2-one derivatives, pharmaceutically acceptable salts thereof, solvates of the derivatives, or solvates of the salts. The present invention further relates to methods for preparing the pyrrolyl substituted dihydroindol-2-one derivatives, pharmaceutical compositions and uses thereof.

BACKGROUND ART

Tumor is one of the major diseases seriously threatening human life and affects the quality of life of the patients. According to the statistic data of World Health Organization (WHO), about 6.9 millions of patients die of tumors around the world each year. Due to the change of living environment and life habits, under the action of harmful environment and some adverse factors, morbidity and mortality of tumors have been increased in recent years.

Formerly, the treatment of tumors is done by finding and destroying the tumors. As the progress of researches in cell signal transduction pathways at present, the understanding of functions of oncogenes and anti-oncogenes in tumor cells is much comprehensive, it draws more attention to the design of new anti-tumor drugs aiming at tumor specific molecular targets. And targeted anti-tumor drugs as new therapies are applied in clinics, and have showen noticeable advances in recent years. It is reported protein tyrosine kinases (PTK) signaling pathway is closely related to the proliferation, differentiation, migration and apoptosis of tumor cells (Sun L., et al., Drug Discov Today, 2000, 5, 344-353), and the use of a protein tyrosine kinase inhibitor to interfere or block tyrosine kinase pathway has been applied to tumor treatment (Fabbro D., et al., Curr Opin Pharmacol, 2002, 2, 374-381).

Protein tyrosine kinase (PTK) is a member of the family of oncoproteins and proto-oncoproteins with important functions in normal and abnormal proliferation. This enzyme is capable of selectively phosphorylating tyrosine residue of different substrates, it catalyzes the γ-phosphate-group transfer of ATP to a tyrosine residue of many important proteins, so as to phosphorylate phenolic hydroxyl group. Protein tyrosine kinases are divided into receptor tyrosine kinases (RTK), non-receptor tyrosine kinases as well as IR and Janus kinases (Robinson D. R., et al., Oncogene, 2000, 19, 5548-5557), most of which are receptor tyrosine kinases (RTK). Receptor tyrosine kinases (RTK) are a group of endogenous protein tyrosine kinases, participate in the regulation of many cell activities, have important roles in transduction of mitogenicity signal in initiating cell replication, regulating the growth and differentiation of cells. All are type I membrane proteins, with similar topological structure. They all have one large glycosylated extracellular ligand binding domain, one hydrophobic single transmembrane domain, and one intracellular tyrosine kinase catalytic structural domain as well as regulatory sequence. It is the selevtive binding of ligand to receptor (such as the binding between epidermal growth factor (EGF) and EGFR) that results in the activation of partial coded receptor kinase in receipt cells, followed by the selective phosphorylation of tyrosine residue in target protein, then eventually leads to the transduction of proliferation signal through cytoplasmic membrane.

Most of cell growth factor receptors contain peptide sequence of tyrosine kinase, the overexpression or activation of different tyrosine kinases can be seen in many tumors, for example, EGFR overexpression is commonly seen in all of epithelial cell tumors; the overexpression of platelet-derived growth factor receptor (PDGFR) is commonly seen in glioma. According to the similarity of peptide sequences and structural features thereof, these receptors are further divided into several families: 1) epidermal growth factor receptor family, including EGFR, HER-2, HER-3, HER-4, etc. The overexpression of these receptors is commonly seen in epithelial cell tumors; 2) insulin receptor family, including insulin receptor, insulin-like growth factor receptor (IGF-R) and insulin relevant receptor (IRR), etc. The overexpression of these receptors is commonly seen in blood cancers; 3) platelet-derived growth factor receptor family (PDGFR), including PDGFR-α, PDGFR-β, CSF-1R, c-Kit, etc. The overexpression of these receptors is commonly seen in brain tumors, blood cancers; 4) fibroblast growth factor receptor (FGFR), including FGFR-1, FGFR-2, FGFR-3, FGFR-4, etc. These receptors play an important role in angiogenesis; 5) vascular endothelial cell growth factor receptor (VEGFR), including VEGFR-1, VEGFR-2, VEGFR-3, which are important positive regulatory factors for angiogenesis. The overexpression of tyrosine kinase receptor in different types of tumors results in abnormal activation of signals in cells thereof, leading to cell transformation, continuous proliferation, promoting generation and development of tumors, inhibiting cell apoptosis, so that targeting tyrosine kinase signaling pathway is a good strategy for developing anti-tumor drugs.

Vascular endothelial growth factor (VEGF) is a growth factor mainly acting on vascular endothelial cells. It has many functions such as promoting endothelial cell proliferation, increasing microvascular permeability, inducing angiogenesis (Hanks S. K., et al., FASEB, 1995, 9, 576-596). At present, known VEGF family includes 6 members: VEGF-A, VEGF-B, VEGF-C, VEGF-D, VEGF-E and PDF. Wherein, VEGF-C is a new member of this VEGF family, which is obtained by separation and purification of human prostatic cancer cell line PC3 using Flt4 affinity chromatography (Joukov V., et al., EMBO J, 1996, 15, 290-298). VEGF-C can specifically activate Flt4 on lymphatic endothelium, so that VEGF-C is also called as lymphocyte growth factor. VEGF-C stimulates the growth of both vascular and lymphatic cells. The receptor of VEGF-C is VEGFR-2, which mainly distributed in vascular endothelial cells, promoting vascular endothelial cell proliferation, migration and vessel growth. The formation and development of tumors can be briefly divided into two stages: a stage of cloning proliferation of tumor cells, followed by a stage of angiopoiesis for promoting tumor continuous growth. VEGF acts on existing vascular endothelial cells and renders them differentiation to form new vessels. The new vessels not only provide a basis of substance exchange for tumor cells, but also enable paracrine secretion of some cell factors to promote the proliferation of tumor cells. And at the same time, due to the lack of integrity of vascular wall in newly generated vessels, endothelial cells are loosely linked between each other, basilar membrane has uneven thickness with breakage or absence, tumor cells may easily enter vessel cavity to result in invasion metastasis via blood flow. Hence, VEGF is closely related to tumor growth and metastasis. VEGF can be detected in many tissues of healthy human body, but its expression level is very low. On the contrary, it is overexpressed in many tumor tissues, especially in solid tumors, like liver cancer, brain cancer, breast cancer, lung cancer and kidney cancer (Samoto K., et al. Cancer Res, 1995, 55, 1189-1193; Ferrara N., Curr Opin Biotech, 2000, 11, 617-624; Shiladitya S., et al. Nature, 2005, 436: 568-572). Since the growth and metastasis of solid tumors depend on new vessels, VEGF is an ideal target for blocking solid tumor angiogenesis. There are two opinions in promoting tumor antiangiogenic researches, 1) health adults usually have relative less new vessels, and thus it is considered that antiangiogenic side effects are negligible; 2) the endothelial cells involve in angiogenic process are normal cells, and do not have unstable genome. This means antiangiogenic treatment would not result in drug-resistance. VEGFR is a diffusible vascular endothelium-specific mitogen and angiogenine receptor, which has critical function in physiological and pathological angiopoiesis processes, can inhibit the apoptosis of endothelial cells. This VEFGR family totally has 3 members, VEGFR1, VEGFR2, VEGFR3. At present, it is widely believed that angiopoiesis induced by VEGF is mediated by VEGF binding to VEGF receptor 2 (VEGFR-2) at vascular endothelial cell surface. After VEGF binds to VEGFR-2, VEGFR-2 forms a dimer which induces phosphorylation mediated by tyrosine kinase, and further activates relevant downstream signal transduction.

Platelet derived growth factors (PDGF) are mainly expressed in fibroblasts, smooth muscle cells, as well as kidney, testis and brain, and closely related to oncogenesis. In most of glioblastoma, there is an autocrine loop formed with PDGF and receptor thereof, including autocrine stimulation of PDGF in tumors. Overexpression or overactivation of PDGF receptor, and stimulating angiogenesis in tumors, all promote tumor growth.

In recent years, scientists are focused on the strategy of for inhibiting cell signal transduction pathway to develop new targeted anti-tumor drugs. Signal transduction inhibitor down-regulates the survival and proliferation signals of tumor cells, promotes cell apoptosis, not through cytotoxic effects. Therefore these types of therapy drugs have high selectivity and low toxicity. At present, a dozen of signal transduction inhibitors have been routinely used in clinic for treating tumors, mainly are tyrosine kinase inhibitor type anti-tumor drugs. Among them, multitarget indolone compounds are relatively well developed, examples including, the marketed multitarget tyrosine kinase inhibitor Sunitinib of Pfizer, the drug BIBF-1120 developed by Boehringer Ingelheim is now in phase III clinical trails, and other SU series of compounds (Abrams T J. Mol Cancer Ther., 2003, 2: 1011-21).

Sunitinib, tradename Sutent, is an indolone type small molecule multitarget RTKIs developed by Pfizer. It has inhibitory actions on many tyrosine kinase receptors, and can simultaneously inhibit targets such as VEGFR (−1, −2, −3), PDGFR-β, c-kit, FLT-3, to achieve anti-tumor effect by specifically blocking these signal transduction pathways. This drug show significant activity of inhibiting angiogenesis and against tumor cells. This drug was approved by FDA of the United State in January, 2006, and showed definite clinical efficacy, and it has obtained permission to be marketed in 61 countries including US, Europe, Japan, South Korea, indicated for gastrointestinal stromal tumor after disease progression on or intolerance to imatinib and advanced renal cell carcinoma.

In addition, WO 2008067756, WO 2008138184, WO 2008138232, WO 2007085188, WO 2005058309 and WO 2006002422 disclose pyrrolyl substituted dihydroindolone derivatives, having activity of inhibiting tyrosine kinases.

Small molecule tyrosine kinase inhibitors as new targeted anti-tumor drugs which open a new window for the treatment and prevention of tumors, and they have slight side effects and good tolerance. Although a dozen of small molecule tyrosine kinase inhibitors have brought great contribution for clinical treatment of tumors now, it is still need of discovering more compounds that have better in vivo activity and/or improved pharmacological properties in comparison with the existing tyrosine kinase inhibitors. Hence, it is still very important to develop new improved or highly effective tyrosine kinase inhibitors and to better understand the relationship between these drugs and known target proteins as well as their anti-tumor mechanisms.

DESCRIPTIONS OF THE INVENTION

The objective of the present invention is to find new compounds with high tyrosine kinase inhibitory effect and relatively low toxicity.

The inventors have surprisingly discovered that the pyrrolyl substituted dihydroindol-2-one derivatives of formula I have unexpectedly high tyrosine kinase inhibitory effect. The present invention is then completed on the basis of this discovery.

One aspect of the present invention relates to a pyrrolyl substituted dihydroindol-2-one derivative of formula I, a pharmaceutically acceptable salt thereof, a solvate of said derivative, or a solvate of said salt,

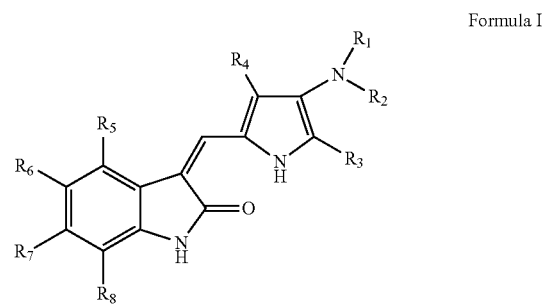

Formula I wherein, $R_1$ is selected from the group consisting of hydrogen atom, $C_{1-4}$ alkyl;

$R_2$ is selected from the group consisting of $C_{1-4}$ alkyl, $C_{1-4}$ alkyl substituted with one or more halogen or hydroxyl groups, allyl, propargyl, $-(CH_2)_mNR_{11}R_{12}$, $-SO_jR_{11}$, $-(CH_2)_mSO_j(CH_2)_nNR_{11}R_{12}$, $-CO(CH_2)_kNR_{11}R_{12}$, $-SO_j(CH_2)_mCH=CH(CH_2)_nNR_{11}R_{12}$, $-CO(CH_2)_mCH=CH(CH_2)_nNR_{11}R_{12}$; wherein $R_{11}$ and $R_{12}$ are each independently selected from the group consisting of hydrogen atom, $C_{1-4}$ alkyl, cycloalkyl, heterocycloalkyl, wherein said cycloalkyl, heterocycloalkyl can be substituted with one or more halogen, alkyl, hydroxy, amino, alkoxy groups; or $R_{11}$, $R_{12}$ together with N atom can form a 4- to 8-membered heterocycle, the heterocycle can further comprise 0 to 2 heteroatoms selected from N, S, O, and the heterocycle can be substituted at any other positions, except S or O atom, and the substituent is selected from the group consisting of $C_{1-4}$ alkyl, hydroxy-substituted $C_{1-4}$ alkyl, $-(CH_2)_mNR_{11}R_{12}$; m, n each independently can be an integer of 0 to 4, k is an integer of 1 to 4, and j is 1 or 2;

$R_3$, $R_4$ are each independently selected from the group consisting of hydrogen atom, halogen, $C_{1-4}$ alkyl;

$R_5$, $R_6$, $R_7$, $R_8$ are each independently selected from the group consisting of hydrogen atom, halogen, $C_{1-4}$ alkyl, $C_{1-4}$ alkyl substituted with one or more halogens, $C_{1-4}$ alkoxy, alkoxy substituted with one or more halogens, cycloalkyl, alkenyl, alkynyl, aryl, heteroaryl, hydroxy, $-NR_9R_{10}$, —SOR$_9$, —SO$_2$R$_9$, —NR$_9$SO$_2$R$_{10}$, —SO$_2$NR$_9$R$_{10}$, —COR$_9$, —NR$_9$COR$_{10}$, —OCOR$_9$, —NO$_2$, wherein the aryl, heteroaryl, cycloalkyl groups can be further substituted at any positions with alkyl, halogen or haloalkyl, alkoxy, haloalkoxy;

R$_9$ and R$_{10}$ are each independently selected from the group consisting of hydrogen atom, C$_{1-4}$ alkyl, C$_{1-4}$ alkyl substituted with one or more halogens, cycloalkyl, aryl or heteroaryl, wherein the cycloalkyl, aryl or heteroaryl can be substituted with one or more halogens, alkyl, hydroxy, amino, or haloalkyl, alkoxy, haloalkoxy;

the above halogens can be independently selected from the group consisting of fluorine, chlorine and bromine.

The term "alkyl" used herein refers to a saturated straight or branched monovalent hydrocarbyl having 1-8 carbon atoms (i.e., C$_{1-8}$ alkyl), preferably 1-6 carbon atoms (i.e., C$_{1-6}$ alkyl), 1-4 carbon atoms (i.e., C$_{1-4}$ alkyl) or 1-3 carbon atoms (i.e., C$_{1-3}$ alkyl). The examples of "alkyl" include but are not limited to methyl, ethyl, n-propyl, iso-propyl, n-butyl, tert-butyl, n-pentyl, neopentyl, n-hexyl, 2-methylpentyl, 2,2-dimethylbutyl, 3,3-dimethylbutyl and so on.

The term "alkenyl" used herein refers to a monovalent olefinic unsaturated hydrocarbyl having 2-8 carbon atoms, preferably 2-6 carbon atoms, which can be a straight or branched chain group and has at least one carbon-carbon double bond. Specific alkenyl includes but is not limited to ethenyl (—CH═CH$_2$), n-propenyl (—CH$_2$CH═CH$_2$), iso-propenyl (—C(CH$_3$)═CH$_2$), butenyl and so on.

The term "alkynyl" used herein refers to a monovalent acetylenic unsaturated hydrocarbyl having 2-8 carbon atoms, preferably 2-6 carbon atoms, which can be a straight or branched chain group and has at least one carbon-carbon triple bond. Specific alkynyl includes but is not limited to ethynyl (—C≡CH), propargyl (—CH$_2$CCH) and so on.

The term "halogen" used herein refers to fluorine, chlorine, bromine or iodine. Preferred halogen group is fluorine, chlorine or bromine.

The term "alkoxy" used herein refers to group —OR$^a$, wherein R$^a$ is alkyl as defined herein. Examples of "alkoxy" include but are not limited to methoxy, ethoxy, n-propoxy, iso-propoxy, n-butoxy, tert-butoxy, n-pentoxy, n-hexoxy, 1,2-dimethylbutoxy and so on.

The term "haloalkyl" used herein refers to an alkyl as defined herein that is mono- or multi-substituted with halogen as defined herein. Examples of "haloalkyl" include but are not limited to —CF$_3$, —CHF$_2$, —CH$_2$CCl$_3$ and so on.

The term "haloalkoxy" used herein refers to an alkoxy as defined herein that is mono- or multi-substituted with halogen as defined herein. Examples of "haloalkoxyl" include but are not limited to —OCF$_3$, —OCHF$_2$, —OCH$_2$CCl$_3$ and so on.

The term "cycloalkyl" used herein refers to a cyclic hydrocarbyl having 3-12 carbon atoms, preferably 3-8 carbon atoms, more preferably 5-6 carbon atoms and having a monocyclic ring or polycyclic fused or bridged ring systems. For example, this kind of cycloalkyl can include: a monocyclic structure, such as cyclopropyl, cyclobutyl, cyclopentyl, cyclooctyl, 1-methylcyclopropyl, 2-methylcyclopentyl, 2-methylcyclooctyl and so on; and a polycyclic structure, such as adamantyl and so on.

The term "heterocycloalkyl" used herein refers to a cycloalkyl as defined herein in which one or more carbon atoms are independently replaced with heteroatoms selected from N, O and S. Examples of heterocycloalkyl include but are not limited to tetrahydropyrrolyl, piperazinyl, piperidyl and morpholinyl and so on.

The term "aryl" used herein refers to an aromatic carbocyclic group having 5-14 carbon atoms and having a monocyclic ring or polycyclic fused rings. The aryl preferably has 5-10, 5-8 or 5-6 or 6 carbon atoms. Examples of "aryl" include but are not limited to phenyl, naphthyl and anthryl and so on.

The term "heteroaryl" used herein refers to a 5- to 14-membered heteroaromatic cyclic group, including monocyclic heteroaryl ring and polycyclic heteroaryl ring. Heteroaryl has one or more ring heteroatoms independently selected from N, O and S. The term "heteroaryl" used herein further includes a group in which an aromatic ring is fused to one or more non-aromatic rings (carbocyclic rings or heterocylic rings), in which the radical or point of attachment is on the aromatic ring. Examples of "heteroaryl" include but are not limited to pyridyl, pyrimidyl, imidazolyl, pyrrolyl, pyrazolyl, oxazolyl, thiazolyl, furyl, benzimidazoyl, benzothiophenyl, benzofuryl, indolyl, benzothiazolyl, benzoxazolyl, quinolyl and so on.

The above pharmaceutically acceptable salt is selected from the group consisting of hydrochloride, sulfate, mesylate, tosylate, benzenesulfonate, fumarate, maleate, malate, or solvates of these salts, such as hydrates.

In one embodiment of the present invention, R$_1$ is hydrogen atom.

In one embodiment of the present invention, R$_5$, R$_6$, R$_7$, R$_8$ are each independently selected from the group consisting of hydrogen atom, halogen, C$_{1-4}$ alkyl, C$_{1-4}$ alkyl substituted with one or more halogens, C$_{1-4}$ alkoxy, C$_{1-4}$ alkoxy substituted with one or more halogens, alkenyl, alkynyl, hydroxy, —NR$_9$R$_{10}$, —SOR$_9$, —SO$_2$R$_9$, —NR$_9$SO$_2$R$_{10}$, —SO$_2$NR$_9$R$_{10}$, —OCOR$_9$, —CN, —NO$_2$.

In one embodiment of the present invention, the pyrrolyl substituted dihydroindol-2-one derivative is selected from the group consisting of the following compounds:

N-{5-[5-fluoro-2-oxo-1,2-dihydro-indol-(3Z)-ylidenemethyl]-2,4-dimethyl-1H-pyrrol-3-yl}-3-(N,N-diethylamino)propionamide;

N-{5-[5-chloro-2-oxo-1,2-dihydro-indol-(3Z)-ylidenemethyl]-2,4-dimethyl-1H-pyrrol-3-yl}-3-(N,N-diethylamino)propionamide;

N-{5-[5-bromo-2-oxo-1,2-dihydro-indol-(3 Z)-ylidenemethyl]-2,4-dimethyl-1H-pyrrol-3-yl}-3-(N,N-diethylamino)propionamide;

N-{5-[5-fluoro-2-oxo-1,2-dihydro-indol-(3Z)-ylidenemethyl]-2,4-dimethyl-1H-pyrrol-3-yl}-4-(N,N-dimethylamino)-(2E)-crotonamide;

N-{5-[5-fluoro-2-oxo-1,2-dihydro-indol-(3Z)-ylidenemethyl]-2,4-dimethyl-1H-pyrrol-3-yl}-4-(N,N-dimethylamino)butyramide;

N-{5-[5-fluoro-2-oxo-1,2-dihydro-indol-(3Z)-ylidenemethyl]-2,4-dimethyl-1H-pyrrol-3-yl}-3-(N,N-dimethylamino)propionamide;

N-{5-[5-fluoro-2-oxo-1,2-dihydro-indol-(3Z)-ylidenemethyl]-2,4-dimethyl-1H-pyrrol-3-yl}-acrylamide;

N-{5-[5-methylsulfonylamino-2-oxo-1,2-dihydro-indol-(3Z)-ylidenemethyl]-2,4-dimethyl-1H-pyrrol-3-yl}-3-(N,N-diethylamino)propionamide;

N-{5-[5-fluoro-2-oxo-1,2-dihydro-indol-(3Z)-ylidenemethyl]-2,4-dimethyl-1H-pyrrol-3-yl}-2-(N,N-diethylamino)ethylsulfonamide;

N-{5-[5-fluoro-2-oxo-1,2-dihydro-indol-(3Z)-ylidenemethyl]-2,4-dimethyl-1H-pyrrol-3-yl}-3-(4-ethylpiperazin-1-yl)propionamide;

N-{5-[5-fluoro-2-oxo-1,2-dihydro-indol-(3Z)-ylidenemethyl]-2,4-dimethyl-1H-pyrrol-3-yl}-3-(4-methylpiperazin-1-yl)propionamide;

N-{5-[5-fluoro-2-oxo-1,2-dihydro-indol-(3Z)-ylidenemethyl]-2,4-dimethyl-1H-pyrrol-3-yl}-3-(morpholin-4-yl)propionamide;
N-{5-[5-fluoro-2-oxo-1,2-dihydro-indol-(3Z)-ylidenemethyl]-2,4-dimethyl-1H-pyrrol-3-yl}-3-(piperidin-1-yl)propionamide;
N-{5-[5-fluoro-2-oxo-1,2-dihydro-indol-(3Z)-ylidenemethyl]-2,4-dimethyl-1H-pyrrol-3-yl}-3-(tetrahydropyrrol-1-yl)propionamide;
N-{5-[5-fluoro-2-oxo-1,2-dihydro-indol-(3Z)-ylidenemethyl]-2,4-dimethyl-1H-pyrrol-3-yl}-2-(4-methylpiperazin-1-yl)acetamide;
N-{5-[5-fluoro-2-oxo-1,2-dihydro-indol-(3Z)-ylidenemethyl]-2,4-dimethyl-1H-pyrrol-3-yl}-2-(piperidin-1-yl)acetamide;
N-{5-[5-fluoro-2-oxo-1,2-dihydro-indol-(3Z)-ylidenemethyl]-2,4-dimethyl-1H-pyrrol-3-yl}-2-(tetrahydropyrrol-1-yl)acetamide;
N-{5-[5-fluoro-2-oxo-1,2-dihydro-indol-(3Z)-ylidenemethyl]-2,4-dimethyl-1H-pyrrol-3-yl}-2-(4-ethylpiperazin-1-yl)acetamide;
N-{5-[5-fluoro-2-oxo-1,2-dihydro-indol-(3Z)-ylidenemethyl]-2,4-dimethyl-1H-pyrrol-3-yl}-2-(morpholin-4-yl)acetamide;
N-{5-[5-fluoro-2-oxo-1,2-dihydro-indol-(3Z)-ylidenemethyl]-2,4-dimethyl-1H-pyrrol-3-yl}-2-(N,N-diethylamino)acetamide;
N-{5-[5-chloro-2-oxo-1,2-dihydro-indol-(3Z)-ylidenemethyl]-2,4-dimethyl-1H-pyrrol-3-yl}-2-(N,N-diethylamino)acetamide;
N-{5-[5-fluoro-2-oxo-1,2-dihydro-indol-(3Z)-ylidenemethyl]-2,4-dimethyl-1H-pyrrol-3-yl}-2-(N,N-dimethylamino)acetamide;
N-{5-[6-methoxy-2-oxo-1,2-dihydro-indol-(3Z)-ylidenemethyl]-2,4-dimethyl-1H-pyrrol-3-yl}-2-(N,N-diethylamino)acetamide;
N-{5-[6-trifluoromethyl-2-oxo-1,2-dihydro-indol-(3Z)-ylidenemethyl]-2,4-dimethyl-1H-pyrrol-3-yl}-2-(N,N-diethylamino)acetamide;
N-{5-[5-methylsulfonylamino-2-oxo-1,2-dihydro-indol-(3Z)-ylidenemethyl]-2,4-dimethyl-1H-pyrrol-3-yl}-2-(N,N-diethylamino)acetamide;
N-{5-[5-nitro-2-oxo-1,2-dihydro-indol-(3Z)-ylidenemethyl]-2,4-dimethyl-1H-pyrrol-3-yl}-2-(N,N-diethylamino)acetamide;
N-{5-[6-methyl-2-oxo-1,2-dihydro-indol-(3Z)-ylidenemethyl]-2,4-dimethyl-1H-pyrrol-3-yl}-2-(N,N-diethylamino)acetamide;
N-{5-[5-acetylamino-2-oxo-1,2-dihydro-indol-(3Z)-ylidenemethyl]-2,4-dimethyl-1H-pyrrol-3-yl}-2-(N,N-diethylamino)acetamide.

In addition, the pyrrolyl substituted dihydroindol-2-one derivative is further selected from the group consisting of the following compounds:

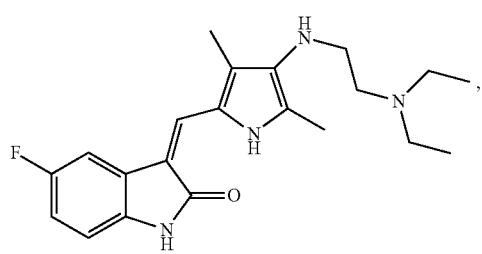

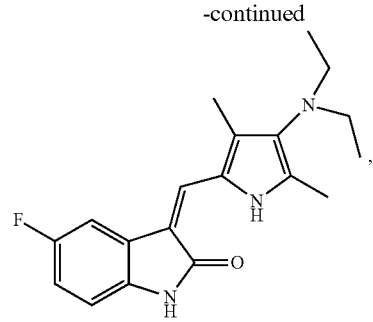

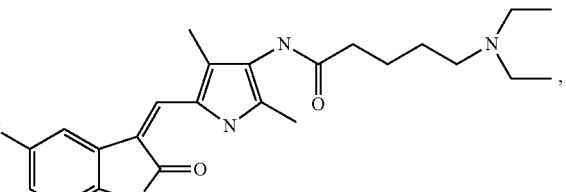

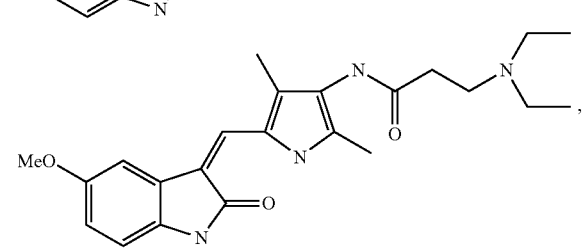

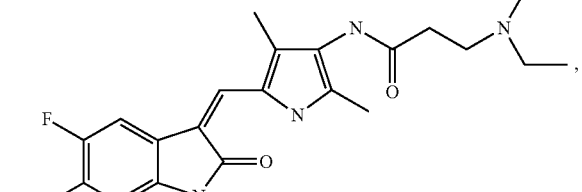

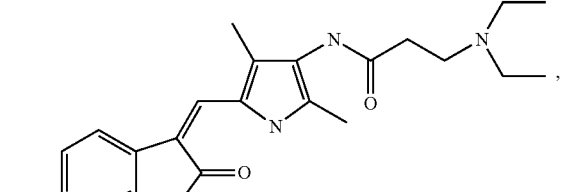

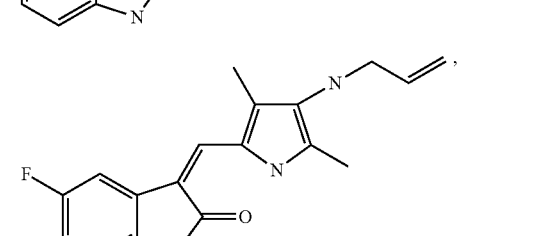

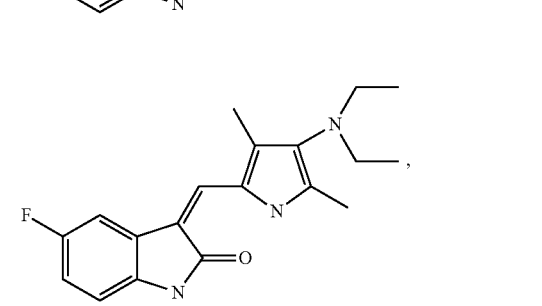

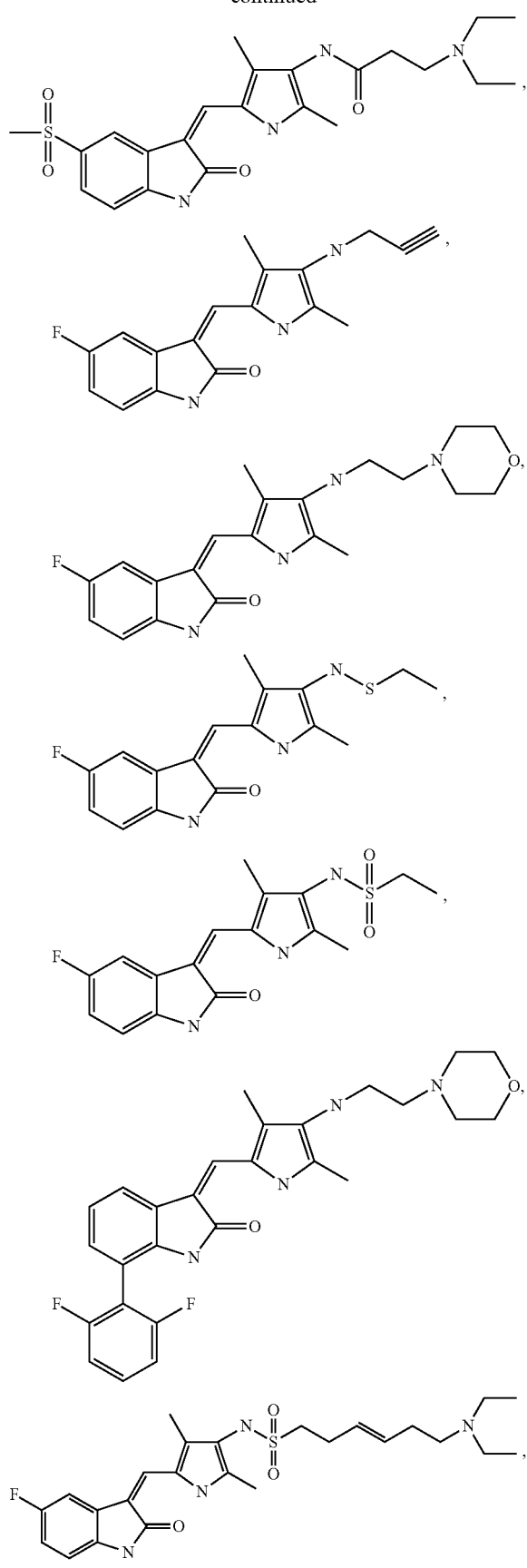

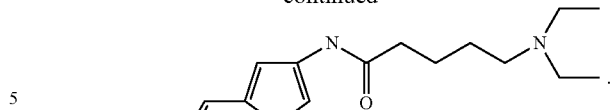

Another aspect of the present invention relates to a pharmaceutical composition, which comprises the above pyrrolyl substituted dihydroindol-2-one derivative, a pharmaceutically acceptable salt thereof, a solvate of said derivative, or a solvate of said salt, and optionally one or more pharmaceutically acceptable carriers and/or excipients.

Further another aspect of the present invention relates to a method for preparing the above pyrrolyl substituted dihydroindol-2-one derivative, comprising the following steps:

1) synthesizing a substituted 4-nitro-2-formylpyrrole compound from suitable raw materials:

synthesizing the substituted 4-nitro-2-formylpyrrole compound directly from substituted 2-formylpyrrole by nitration using a suitable nitrating agent:

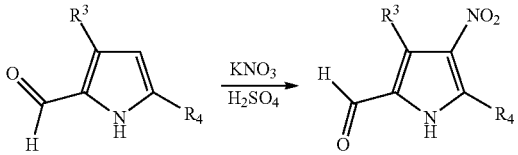

or synthesizing the substituted 4-nitro-2-formylpyrrole compound indirectly from 2-ester group substituted pyrrole via nitration, decarboxylation and oxidization:

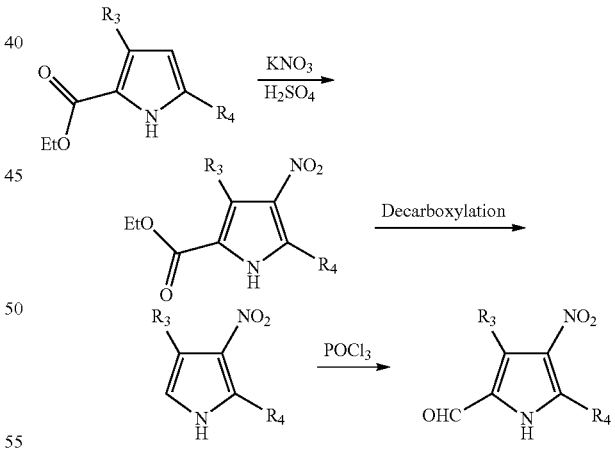

2) synthesizing compound A from the substituted 4-nitro-2-formylpyrrole compound:

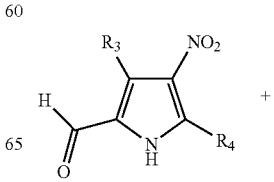

-continued

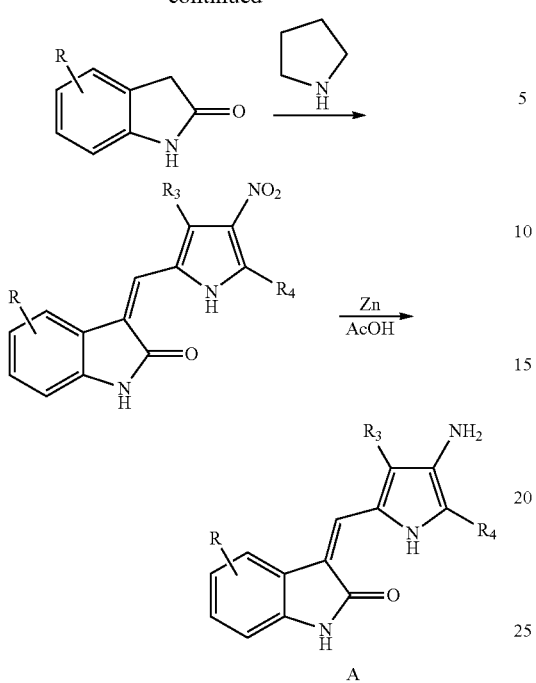

3) synthesizing the target compound directly from compound A and a corresponding raw material via a suitable reaction:

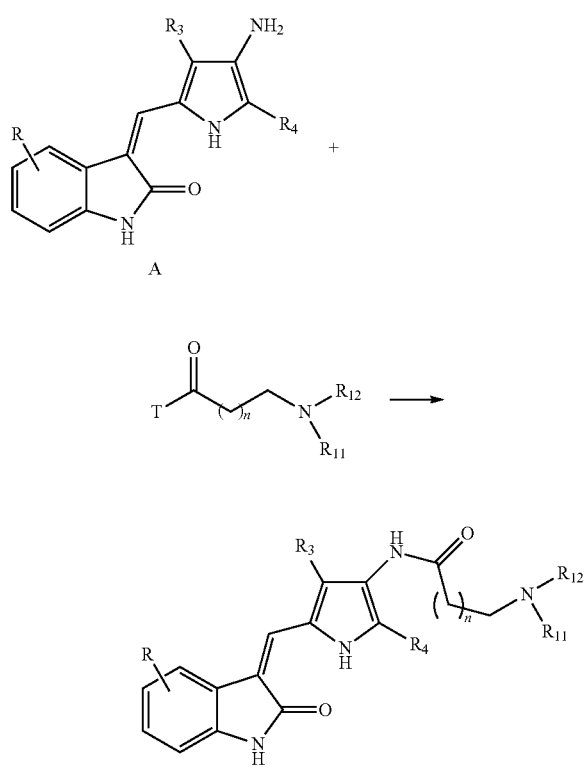

or synthesizing a corresponding halogenated intermediate B first from compound A, and then synthesizing the target compound via a further step of reaction:

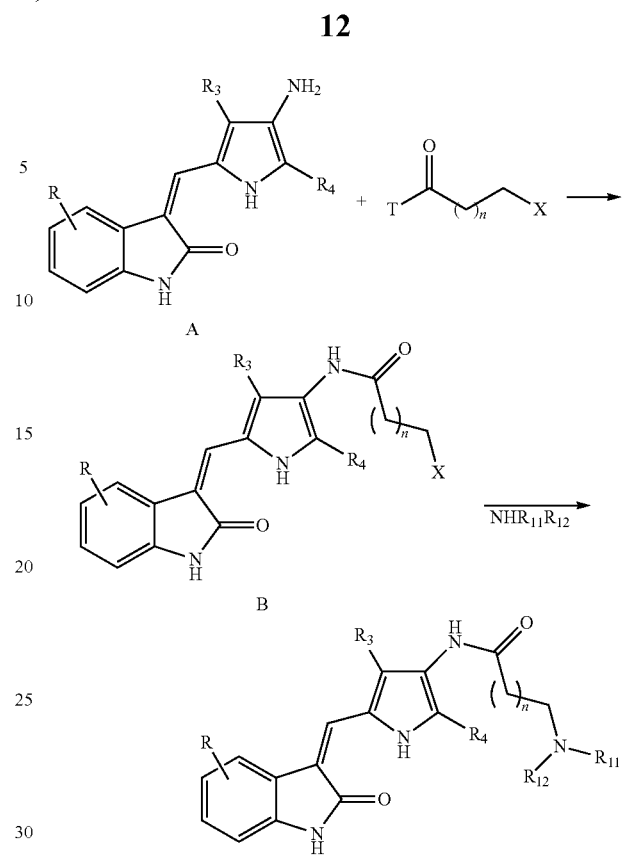

wherein, $R_3$, $R_4$, $R_{11}$, $R_{12}$ are those as described in the above formula I; X is selected from the group consisting of Cl, Br or I, preferably Cl or Br; R is optionally selected from one or more of $R_5$—$R_8$ as defined in the above formula I; n is an integer of 0 to 4, and T is selected from the group consisting of OH or Cl.

Further another aspect of the present invention relates to use of the above pyrrolyl substituted dihydroindol-2-one derivative, a pharmaceutically acceptable salt thereof, a solvate of said derivative, or a solvate of said salt for the manufacturing of a tyrosine kinase inhibitor.

Further another aspect of the present invention relates to use of the above pyrrolyl substituted dihydroindol-2-one derivative, a pharmaceutically acceptable salt thereof, a solvate of said derivative, or a solvate of said salt for the manufacturing of a medicament for the treatment and/or prevention of diseases associated with receptor tyrosine kinase in a mammal. Specifically, the mammal is a human.

Further another aspect of the present invention relates to use of the above pyrrolyl substituted dihydroindol-2-one derivative, a pharmaceutically acceptable salt thereof, a solvate of said derivative, or a solvate of said salt for the manufacturing of a medicament for the treatment or adjunctive treatment and/or prevention of a tumor mediated by receptor tyrosine kinase or tumor cell proliferation and migration driven by receptor tyrosine kinase in a mammal. Specifically, the mammal is a human.

According to the present invention, it can be fully expected that the compound of the present invention can be used for treating VEGFR or PDGFR tyrosine kinase sensitive cancers, for example, tumors with overexpressed VEGFR, PDGFR and VEGF promoted tumor types, including solid tumors such as cancers of bile duct, bone, bladder, brain/central nervous system, breast, colon and rectum, endometrium, stomach, head and neck, liver, lung (especially non-cell lung cancer), neuron, esophagus, ovary, pancreas, prostate, kidney, skin, testis, thyroid, uterus and vulva and so on, and non-solid tumors such as leukemia, multiple myeloma or lymphoma, etc. The derivatives of the present invention can regulate protein kinase activity and can be used for the prevention and treatment of cell dysfunction associated with protein kinase, so that the compounds of the present invention can further be used for the prevention and treatment of dysfunctions related to abnormal protein kinase activities.

Further another aspect of the present invention relates to a method of treating and/or preventing diseases associated with tyrosine kinase in a mammal comprising administering an effective amount of the pyrrolyl substituted dihydroindol-2-one derivative, a pharmaceutically acceptable salt thereof, a solvate of said derivative, or a solvate of said salt of the present invention, or the pharmaceutical composition of the present invention.

Further aspect of the present invention relates to a method of treatment or adjunctive treatment and/or prevention of a tumor mediated by tyrosine kinase or tumor cell proliferation and migration driven by tyrosine kinase in a mammal (including human) comprising administering an effective amount of the pyrrolyl substituted dihydroindol-2-one derivative, a pharmaceutically acceptable salt thereof, a solvate of said derivative, or a solvate of said salt of the present invention, or the pharmaceutical composition of the present invention.

Further another aspect of the present invention relates to a method of treating and/or preventing a tumor or cancer in a mammal (including human) comprising administering the mammal in such need an effective amount of the pyrrolyl substituted dihydroindol-2-one derivative, a pharmaceutically acceptable salt thereof, a solvate of said derivative, or a solvate of said salt of the present invention, or the pharmaceutical composition of the present invention. The tumor or cancer includes VEGFR or PDGFR tyrosine kinase sensitive cancers, for example, tumors with overexpressed VEGFR, PDGFR and VEGF promoted tumor types, including solid tumors such as cancers of bile duct, bone, bladder, brain/central nervous system, breast, colon and rectum, endometrium, stomach, head and neck, liver, lung (especially non-cell lung cancer), neuron, esophagus, ovary, pancreas, prostate, kidney, skin, testis, thyroid, uterus and vulva and so on, and non-solid tumors such as leukemia, multiple myeloma or lymphoma, etc.

The present invention is further illustrated as follows.

All documents as cited in the present invention are incorporated in the text by reference, and if the meanings of these documents are inconsistent with the present invention, the expressions of the present invention should be used. In addition, the terms and phrases used in the present invention has common meanings well known by those skilled in the art, nevertheless, these terms and phrases are further explained and illustrated in the invention. If the mentioned terms and phrases have meanings different from those known in the art, the meanings present in the present invention should be used.

In the methods for synthesis of the compound of formula I of the present invention, all raw materials used for reaction can be prepared and obtained by those skilled in the art according to the knowledge in the art, or can be obtained by the methods well known in the art, or can be obtained commercially. The intermediates, raw materials, reagents and reaction conditions used in the above reaction schemes can be suitably changed by those skilled in the art according to the knowledge in the art. Or, those skilled in the art can also synthesize those not specifically illustrated compounds of formula I according to the method of the second aspect of the present invention.

The compound of formula I of the present invention can be used in combination with another active ingredient, as long as it does not result in adverse effects such as anaphylactic response.

The active compounds of formula I of the present invention can be used by itself as anticancer drug, or can be used in combination with one or more other anti-tumor drugs. The combination therapy is carried out by administering these therapeutic components simultaneously, in sequence, or separately.

The term "composition" used herein refers to a product comprising designated components in designated amounts, and any products directly or indirectly formed with the designated components in designated amounts.

The compounds of the present invention can be used in form of pharmaceutically acceptable salts derived from inorganic acids or organic acids. The term "pharmaceutically acceptable salt" refers to a salt which is suitable for contacting tissues of human and lower animals without showing excessive toxicity, irritation, anaphylactic response within range of reliable medical judgment, and is commensurate to reasonable effect/risk ratio. The pharmaceutically acceptable salt is well known in the art. For example, S. M. Berge, et al., J. Pharmaceutical Sciences, 1977, 66: 1 describes pharmaceutically acceptable salts in details. The salts can be in situ prepared in the final separation and purification process of the compounds of the present invention or prepared alone by reacting the free basic functional groups of the compounds of the present with a suitable organic acid. The typical acid addition salts include but are not limited to acetate, adipate, alginate, citrate, aspartate, benzoate, benzenesulfonate, bisulfate, butyrate, camphorate, camphor sulfonate, digluconate, glycerophosphate, hemisulfate, heptylate, caproate, fumarate, hydrochloride, hydrobromide, hydroiodide, 2-hydroxyesylate (isothionate), lactate, maleate, mesylate, nicotinate, 2-napsylate, oxalate, palmate, pectate, persulfate, 3-phenylpropionate, picrate, pivalate, propionate, succinate, tartrate, thiocyanide, phosphate, glutamate, bicarbonate, p-tosylate and undecanoate. Likewise, alkaline nitrogen-containing group can be quaternized with the following substances: low alkyl halogenides such as chlorides, bromides and iodides of ethyl, propyl and butyl; dialkyl sulfates such as dimethyl sulfate, diethyl sulfate, dibutyl sulfate and dipentyl sulfate; long chain halogenides such as chlorides, bromides and iodides of decyl, dodecyl, tetradecyl and octadecyl; arylalkyl halogenides such as benzyl bromide, phenylethyl bromide and so on.

The compounds of formula I of the present invention further comprise isomers, racemates, enantiomers, diastereomers, enantiomer-enriched products, solvates, and esters thereof, and the compounds of formula I of the present invention and isomers, racemates, enantiomers, diastereomers, enantiomers-enriched products, solvates and esters thereof can further form solvates, such as hydrates, alcoholates, etc. The compounds can further be prodrugs or a form capable of releasing the active ingredient after in vivo metabolism. It is common knowledge for a skilled in the art to select and prepare a suitable prodrug derivative. Generally, for the purpose of the present invention, solvates of the pharmaceutically acceptable solvents such as water, ethanol and so on are comparable to those not in form of solvates.

The actual dose level of various active ingredients in a pharmaceutical composition of the present invention can be varied so that the resultant amount of active compounds can lead to desired therapeutic reactions in specific patients, dosage forms and administration modes. The dose level must be determined according to the activity of specific compound, administration route, severity of disease to be treated, and conditions and past medical history of patients. However, a conventional method in the art is to increase gradually the dose of compound from a level lower than that for achieving desired therapeutic effects to a level enough to achieve the desired therapeutic effects.

In the aforementioned or other treatment and/or prevention, a compound of the present invention in a therapeutically and/or preventively effective amount can be used in form of pure compound, or in form of pharmaceutically acceptable esters or prodrugs thereof (if they exist). Alternatively, the compound can be administered via a pharmaceutical composition comprising the compound and one or more pharmaceutically acceptable excipients. The term of a compound of the present invention in a "therapeutically and/or preventively effective amount" means that the compound is in an amount sufficient to achieve preventively and/or therapeutically reasonable ratio of effect/risk. It should be understood that the total amount per day of the compound or composition of the present invention must be determined by a physician within the range of reliable medical decisions. As for any specific patients, the specific therapeutically amount must be determined based on various factors, including the diseases to be treated and severity thereof, the activity of the used specific compound, the used specific composition, the age, body weight, general health status, gender and food of patient, the administration time and route and excretory rate of the used specific compound, the drug(s) administered in combination or simultaneously with the specific compound, and similar factors well known in the art of medicine. For example, it is a common method in the art to increase gradually the dose of compound from a level lower than that for achieving desired therapeutic effects to a level enough to achieve the desired therapeutic effects. In general, the dose of a compound of formula I for mammals especially human can be 0.001-1000 mg/kg body weight per day, such as 0.01-100 mg/kg body weight per day, 0.01-10 mg/kg body weight per day.

A pharmaceutical composition comprising an effective amount of the compound of the present invention can be prepared by using a pharmaceutically acceptable carrier well-known by those skilled in the art. Hence, the present invention further provides a pharmaceutical composition comprising the compound of the present invention formulated with one or more non-toxic pharmaceutically acceptable carriers. The pharmaceutical composition can be specifically formulated in solid or liquid form for oral administration, parenteral injection or rectal administration.

The pharmaceutical composition can be formulated in many dosage forms for facilitating administration, for example, oral preparations (such as tablets, capsules, solutions or suspensions); injectable preparations (such as injectable solutions or suspensions, or injectable dry powders that can be immediately used by adding water before injection). The carrier in the pharmaceutical composition comprises for oral preparations: binders (such as starch, typically being starches of corn, wheat or rice, gelatin, methylcellulose, sodium carboxymethylcellulose and/or polyvinylpyrrolidone), diluents (such as lactose, dextrose, sucrose, mannitol, sorbitol, cellulose, and/or glycerol), lubricants (such as silica, talc, stearic acid or salts thereof, typically being magnesium stearate or calcium stearate, and/or polyethylene glycol), if desired, further comprises disintegrating agents such as starch, agar, alginic acid or salts thereof, typically sodium alginate, and/or effervescence mixtures, co-solvents, stabilizing agents, suspending agents, pigments, correctants, etc.; for injectable preparations: preservatives, solubilizing agents, etc.; for topical preparations: substrates, diluents, lubricants, preservatives, etc. The pharmaceutical preparations can be administered orally or parenterally (such as intravenously, subcutaneously or topically), and if some drugs are not stable in gastral conditions, they can be formulated in coating tablets.

More specifically, the pharmaceutical composition of the present invention can be adminstered orally, rectally, parenterally, rectally, parenterally, endoluminally, endovaginally, intraperitoneally, topically (such as via powder, ointment or drops), buccally to a human or other mammal, or administrated as oral spray or nasal spray. The term "parenteral" in the context refers to administration manners including intravenous, intramusculary, intraperitoneal, intrathoracic, subcutaneous and intraarticular injection or transfusion.

The composition suitable for parenteral injection can comprise physiologically acceptable sterile aqueous or nonaqueous solvent, dispersant, suspending agent, or emulsifying agent, as well as sterile dispersant for reforming a sterile injectable solution or dispersion. The examples of suitable aqueous or nonaqueous carriers, diluents, solvents or media include water, ethanol, polyols (propylene glycol, polyethylene glycol, glycerol, etc), vegetable oil (such as olive oil), injectable organic esters such as ethyl oleate and suitable mixtures thereof.

These compositions can further comprise excipients, such as preservative, wetting agent, emulsifying agent and dispersant. The use of various antibacterial agents and antifungal agents, such as nipagins, nautisan, phenol, sorbic acid, etc. can ensure effects of combating microorganisms. It is also desired to comprise isotonizing agents such as sugars, sodium chloride, etc. The use of substances for absorption delay, such as aluminium monostearate and gelatin, can achieve the prolonged absorption of injectable dosage form.

Besides active compound, the suspension can further comprise suspending agent, such as ethoxylated isooctadecanol, polyoxyethylene sorbitol and polyoxyethylene sorbitan, microcrystalline cellulose, meta-aluminum hydroxide, bentonite, agar and tragacanth gum, or mixtures of these substances.

In some cases, it is desired to reduce the absorption rate of subcutaneously or intramuscularly administered drug for prolonging the effect of drug. This can be achieved by using a liquid suspension of crystal or amorphous form with poor water solubility. Thus, the absorption rate of drug depends on its dissolution rate, while the dissolution rate depends on the size and form of crystal. Or, the delayed absorption of drug in parenteral administration can be achieved by dissolving or dispersing the drug in an oil medium.

A injectable depot dosage form can be prepared by forming microcapsule substrate of drug in a biodegradable polymer such as polylactide-polyglycolide. The release rate of drug can be controlled according to the ratio of drug to polymer and the properties of the spcifically used polymer. Other examples of biodegradable polymer comprise poly(orthoesters) and poly(anhydrides). The injectable depot dosage form can also be prepared by embedding drug in a liposome or microemulsion compatible to body tissues.

The injectable preparation can be sterilized by filtration using a bacterial filter or by incorporating a sterilizing agent in form of sterile solid composition, and the solid composition can be dissolved or dispersed in sterile water or other sterile injectable media before clinical application.

The compound of the present invention or composition thereof can be administered orally or parenterally. Those for oral administration can be tablets, capsules, coated dosage form, and pharmaceutical preparations for parenteral administration can be injections and suppository. These preparations are prepared according to methods well-known by those skilled in the art. In order to manufacture tablets, capsules and coated dosage forms, the used excipients are commonly used excipients, such as starch, gelatin, arabic gum, silica, polyethylene glycol, the solvents used for liquid dosage forms are water, ethanol, propylene glycol, vegetable oils (such as corn oil, peanut oil, oliver oil, etc.). The preparations comprising the compound of the present invention can further comprise other excipients, such as surfactants, lubricants, disintegrants, preservatives, correctants and pigments, etc. In tablets, capsules, coated dosage forms, injections and suppositories, the dose of the compound of formula I of the present invention is expressed in an amount of the compound existed in unit dosage form. In unit dosage form, the amount of the compound of formula I of the present invention usually is 1-5000 mg, a preferable unit dosage form contains 10-500 mg, a more preferable unit dosage form contains 20-300 mg. Specifically, the solid dosage form for oral administration as provided in the present invention comprise capsules, tablets, pills, powders and granules. In such solid dosage forms, the active compound can be mixed with at least one inert pharmaceutically acceptable excipient or carrier such as sodium citrate or dicalcium phosphate and/or the following substances: a) filler or bulking agent, such as starch, lactose, sucrose, glucose, mannitol and silicic acid; b) binding agent, such as carboxymethyl cellulose, alginate, gelatin, polyvinyl pyrrolidone, sucrose, and arabic gum; c) humectant, such as glycerol; d) disintegrating agent, such as agar, calcium carbonate, potato or cassaya starch, alginic acid, some silicates and sodium carbonate; e) solution blocking agent, such as paraffin wax; f) absorption accelerator, such as quaternary ammonium compounds; g) wetting agent, such as cetanol and glycerol monostearate; h) adsorbent, such as kaolin and bentonite; and i) lubricant, such as talc powder, calcium stearate, magnesium stearate, solid polyethylene glycol, sodium dodecylsulfate and their mixtures. In the cases of capsules, tablets and pills, these dosage forms may also comprise a buffering agent.

A solid composition of similar type uses excipients such as lactose and high molecular weight polyethylene glycol which can also be used as fillers of soft capsules and hard capsules.

The solid dosage forms of tablets, dragees, capsules, pills and granules can be prepared with coating agents and shell materials such as enteric coating materials and other coating materials well-known in the field of medical preparations. These solid dosage forms can optionally comprise sunscreening agent, and their composition can allow they merely or preferentially release active ingredient at some sites of intestinal tract optionally in a delayed manner. Examples of embedding composition comprise high molecular materials and waxes. If appropriate, the active compound can be formulated in form of microcapsules with one or more aforementioned excipients.

The liquid dosage form for oral administration comprises pharmaceutically acceptable emulsifying agent, solvent, suspending agent, syrup and elixir. Besides the active compound, the liquid dosage form may further comprise an inert diluent commonly used in the art, such as water or other solvent, solubilizer and emulsifying agent, such as ethanol, isopropanol, ethyl carbonate, ethyl acetate, benzyl alcohol, benzyl benzoate, propylene glycol, butane-1,3-diol, dimethyl formamide, oils (such as cottonseed oil, peanut oil, corn oil, embryo oil, olive oil, castor oil, and sesame oil), glycerol, tetrahydrofurfuryl alcohol, fatty acid esters of polyethylene glycol and sorbitan, and their mixtures. Besides inert diluents, the compositions for oral administration can further comprise excipients, such as wetting agents, emulsifying agents and suspending agents, sweeting agents, correctants and flavors.

The composition for rectal or vaginal administration is preferably a suppository. The suppository can be prepared by mixing the compound of the present invention with a suitable non-irritative excipient or carrier, such as cocoa butter, polyethylene glycol or suppository wax, they can be solid at room temperature, but liquid at body temperature, and can release active compound in rectal lumen or vaginal canal.

It is also desired to use the compound of the present invention for topical administration. The dosage form of the compound of the present invention for topical administration comprises powder, spray, ointment and inhalation. The active compound and a pharmaceutically acceptable carrier can be mixed under sterile conditions with any desired preservative, buffering agent or propellant. Ophthalmic preparation, eye salve, powder and solution are all in the scope of the present invention.

The compound of the present invention can be administered in form of liposome. It is well known in the art, liposome usually is prepared by using phospholipid or other lipids. Liposome is formed with monolayer or multilayer hydrated liquid crystal which is dispersed in an aqueous medium. Any non-toxic, physiologically acceptable and metabolizable lipids capable of forming liposome can be usable. The composition of the present invention in liposome form can comprise stabilizing agent, preservative, excipient, besides the compound of the present invention. Preferable lipids are natural and synthetical phospholipids and phosphatidylcholines (lecithin), they can be used solely or together. The methods for forming liposome are well-known in the art. References can be seen, for example, Prescott, Ed., Methods in Cell Biology, Volume XIV, Academic Press, New York, N.Y. (1976), p. 33.

The inventors have surprisingly found that some of the pyrrolyl substituted dihydroindol-2-one derivatives of formula I have better activity against angiogenesis and relatively low cytotoxicity in rat arterial ring tests and cytotoxicity tests. The inventors have also found in nude mice transplantation tumor test that these compounds have better activity in vivo, and some of the compounds have inhibitory actions on tumor comparable to or superior to the positive control Sunitinib. In addition, analysis of mortality rate of animals shows that some of the compounds having relatively good activity exhibit lower toxicity than the positive control Sunitinib. Specifically, the compounds of the present invention can be used for the prevention or treatment of VEGFR or PDGFR tyrosine kinase sensitive cancers, for example, tumors with overexpressed VEGFR, PDGFR and VEGF promoted tumor types, including solid tumors such as cancers of bile duct, bone, bladder, brain/central nervous system, breast, colon and rectum, endometrium, stomach, head and neck, liver, lung (especially non-cell lung cancer), neuron, esophagus, ovary, pancreas, prostate, kidney, skin, testis, thyroid, uterus and vulva and so on, and non-solid tumors such as leukemia, multiple myeloma or lymphoma, etc.

EXAMPLES FOR CARRYING OUT THE INVENTION

The present invention is further illustrated with specific preparation examples and biological test examples, and it should be understood that these examples and test examples are merely used for detailed illustration but not for limiting the present invention in any way.

The materials and methods used in examples are generally and/or specifically described in the present invention.

Although many materials and operation methods used for fulfilling the purpose of the present invention are known in the art, they are still described in details as much as possible. Those skilled in the art clearly know that if not described particularly, the materials and methods used in the present invention are well known in the art.

In the present invention, unless described otherwise, (i) temperature is expressed in centi-degree (° C.), and operations are performed at room temperature or ambient temperature; (ii) organic solvent is dried with anhydrous sodium sulfate, and the evaporation of solvent is performed by using a rotary evaporator under vacuum and a bath temperature of not higher than 60° C.; (iii) reaction procedure is monitored by using thin-layer chromatograph (TLC); (iv) the final products have satisfactory proton magnetic resonance spectrum ($^1$H-NMR) and mass spectrum (MS) data.

Example 1

Synthesis of N-{5-[5-fluoro-2-oxo-1,2-dihydro-indol-(3Z)-ylidenemethyl]-2,4-dimethyl-1H-pyrrol-3-yl}-3-(N,N-diethylamino)propionamide Compound 1

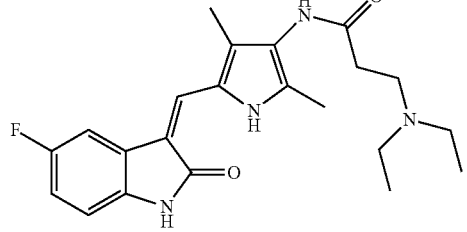

a. Synthesis of 2-formyl-3,5-dimethyl-4-nitro-1-hydropyrrole

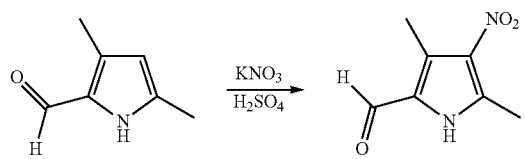

Starting material 2-formyl-3,5-dimethyl-1-hydropyrrole (5.0 g, 1.0e) was added in portions to concentrated sulfuric acid (60 ml), kept at a temperature of 0 to −5° C. The mixture was a reddish brown clear liquid, to which was added potassium nitrate (4.35 g, 1.05 e) in portions, kept at a temperature of −8 to −2° C. After the addition, the mixture was reacted at about −7° C. for 20 min, then was warmed to room temperature and reacted for 20 min. Once the reaction was completed as indicated by TLC, the reaction solution was added into 1500 ml of ice water, and an earthy yellow solid was precipitated. The precipitate was collected by filtration, washed with water to neutral, and dried to obtain a grey product, 6.7 g (yield 98%).

b. Synthesis of (3Z)-[(3,5-dimethyl-4-nitro-1-hydropyrrol-2-yl)methylene]-5-fluoro-indol-2-one

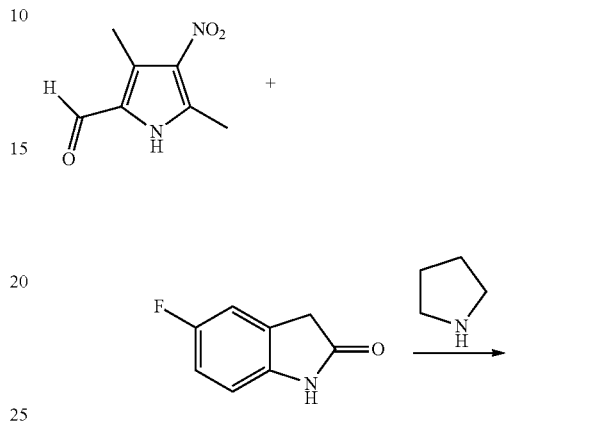

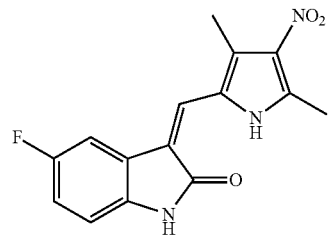

Starting material 2-formyl-3,5-dimethyl-4-nitro-1-hydropyrrole (0.75 g, 1.0 e) and 5-fluoro-indol-2-one (1.0 g, 1.2 e) were added to 20 ml of anhydrous ethanol, to which was added tetrahydropyrrole (1.2 e) under stirring and then the mixture was warmed and reacted at reflux. An orange red solid was precipitated out as the reaction proceeded (when reaction became viscous and thick, a suitable amount of anhydrous ethanol could be added). Once the reaction was completed as indicated by TLC, the reaction mixture was cooled to room temperature, filtered, washed with ethanol and ethyl acetate, and dried to obtain the target product, 1.3 g (yield 96%).

c. Synthesis of (3Z)-[(3,5-dimethyl-4-amino-1-hydropyrrol-2-yl)methylene]-5-fluoro-indol-2-one

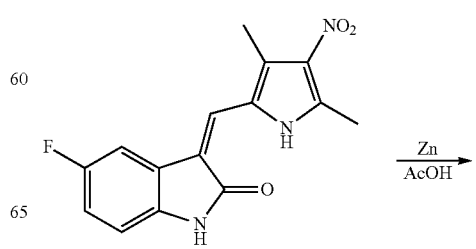

-continued

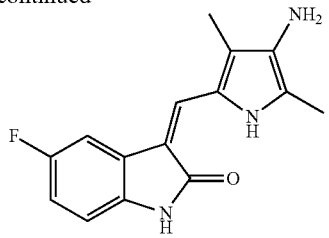

Starting material (3Z)-[(3,5-dimethyl-4-nitro-1-hydropyrrol-2-yl)methylene]-5-fluoro-indol-2-one (1 g) was added to a mixed solvent of ethanol/ethyl acetate (100 ml/50 ml), to which was added zinc powder (2.16 g, about 10 e) and acetic acid (20 ml) with stirring and then the mixture was warmed and reacted at 50° C. The reaction mixture turned to a reddish brown turbid solution. Once the reaction was completed as indicated by TLC, the reaction mixture was cooled to room temperature, to which was added 20 ml of ethyl acetate. Solid product was formed, collected by filtration, washed with small amount of ethanol and ethyl acetate. The filter cake was dissolved in 100 ml of ethyl acetate, washed with saturated sodium carbonate to basic, and then washed with water and saturated sodium chloride, and dried with anhydrous sodium sulfate. The drying agent was filtered off, and the filtrate was concentrated to a reddish brown solid, 0.63 g (yield 70%).

$^1$H-NMR (600 MHz, DMSO-d$_6$, $\delta_{ppm}$): 13.56 (s, 1H), 7.58 (d, 1H, J=9.0), 7.46 (s, 1H), 6.79 (m, 1H), 6.78 (m, 1H), 2.24 (s, 3H), 2.14 (s, 3H).

ESI-MS: [M+H]$^+$ 272, [M−H]$^−$ 270.

d. Synthesis of N-{5-[5-fluoro-2-oxo-1,2-dihydro-indol-(3Z)-ylidenemethyl]-2,4-dimethyl-1H-pyrrol-3-yl}-3-(N,N-diethylamino)propionamide

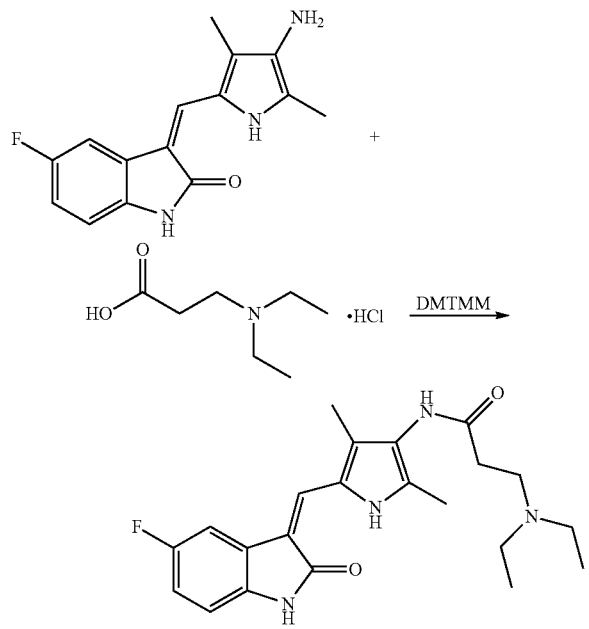

Starting material (3Z)-[(3,5-dimethyl-4-amino-1-hydropyrrol-2-yl)methylene]-5-fluoro-indol-2-one (0.5 g, 1.0 e) was dissolved in 10 ml of DMF, to which was added 3-(N,N-diethylamino)propionic acid hydrochloride (0.37 g, 1.1 e). The mixture was stirred and reacted for 10 min, to which was added 4-(4,6-dimethoxytriazine) chlorinated 4-methylmorpholine (DMTMM) (0.6 g, 1.1 e). Once the reaction was completed as indicated by TLC, the reaction solution was added to 500 ml of ethyl acetate. Solid product was formed, collected by filtration, washed with ethyl acetate, dried, and purified by column chromatograph to obtain the target product, 0.5 g (yield 68%).

$^1$H-NMR (600 MHz, DMSO-d$_6$, $\delta_{ppm}$): 13.56 (s, 1H), 10.85 (s, 1H), 9.36 (s, 1H), 7.69 (d, 1H, J=9.0), 7.65 (s, 1H), 6.89 (m, 1H), 6.84 (m, 1H), 2.97 (m, 2H), 2.90 (m, 4H), 2.19 (s, 3H), 2.16 (s, 3H), 1.04 (m, 6H).

ESI-MS: [M+H]$^+$ 399, [2M+H]$^+$ 797.

Example 2

Synthesis of N-{5-[5-chloro-2-oxo-1,2-dihydro-indol-(3Z)-ylidenemethyl]-2,4-dimethyl-1H-pyrrol-3-yl}-3-(N,N-diethylamino)propionamide

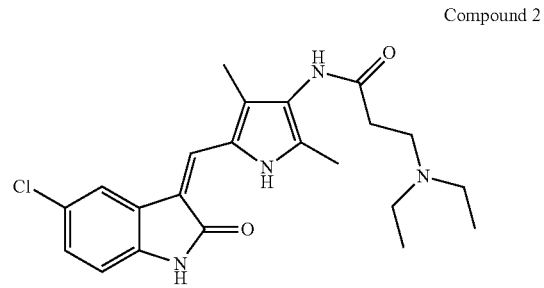 [SMILES: CCN(CC)CCC(=O)Nc1c(C)[nH]c(/C=C2\C(=O)Nc3ccc(Cl)cc32)c1C]

The reaction steps are similar to the steps described in Example 1 in which 5-chloro-indol-2-one was used as the starting material, to obtain Compound 2.

ESI-MS: [M+H]$^+$ 415, [2M+H]$^+$ 829.

Example 3

Synthesis of N-{5-[5-bromo-2-oxo-1,2-dihydro-indol-(3Z)-ylidenemethyl]-2,4-dimethyl-1H-pyrrol-3-yl}-3-(N,N-diethylamino)propionamide

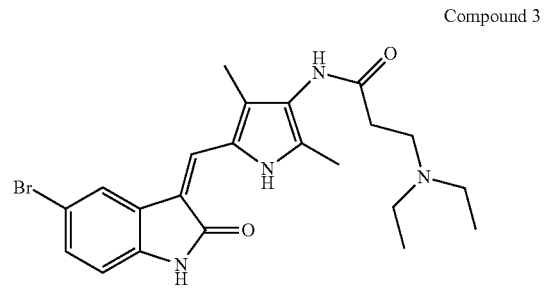

The reaction steps are similar to the steps described in Example 1, in which 5-bromo-indol-2-one was used as the starting material, to obtain Compound 3.

$^1$H-NMR (600 MHz, DMSO-d$_6$, $\delta_{ppm}$): 13.54 (s, 1H), 10.94 (s, 1H), 10.36 (s, 1H), 9.54 (s, 1H), 8.03 (d, 1H, J=1.2), 7.71 (s, 1H), 7.22 (dd, 1H, J$_1$=1.2, J$_2$=8.4), 6.83 (d, 1H, J=8.4), 3.38 (m, 2H), 3.14 (m, 4H), 2.88 (t, 2H), 2.22 (s, 3H), 2.19 (s, 3H), 1.25 (t, 6H).

ESI-MS: [M+H]$^+$ 459, [M−H]$^−$ 457.

Example 4

Synthesis of N-{5-[5-fluoro-2-oxo-1,2-dihydro-indol-(3Z)-ylidenemethyl]-2,4-dimethyl-1H-pyrrol-3-yl}-4-(N,N-dimethylamino)-(2E)-crotonamide

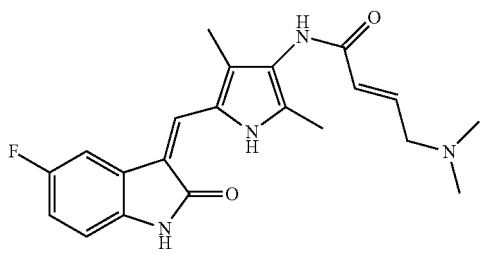

Compound 4

The reaction steps are similar to the steps described in Example 1, in which trans-N,N-dimethylaminocrotonic acid hydrochloride was used as the starting material, to obtain Compound 4.

$^1$H-NMR (600 MHz, DMSO-d$_6$, $\delta_{ppm}$): 13.61 (s, 1H), 10.82 (s, 1H), 9.31 (s, 1H), 7.72 (m, 1H), 7.65 (s, 1H), 6.90 (m, 1H), 6.85 (m, 1H), 6.68 (m, 1H), 6.27 (d, 1H, J=15.0), 3.08 (m, 2H), 2.20 (s, 3H), 2.17 (s, 3H), 1.16 (m, 6H).

ESI-MS: [M+H]$^+$ 383, [2M+H]$^+$ 765.

Example 5

Synthesis of N-{5-[5-fluoro-2-oxo-1,2-dihydro-indol-(3Z)-ylidenemethyl]-2,4-dimethyl-1H-pyrrol-3-yl}-4-(N,N-dimethylamino)butyramide

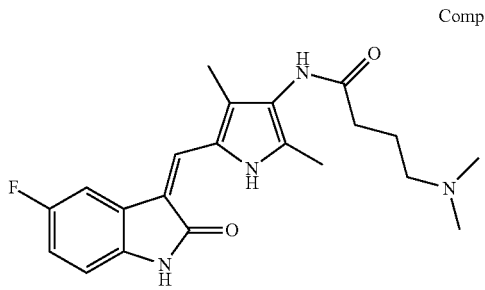

Compound 5

The reaction steps are similar to the steps described in Example 1, in which 4-(N,N-dimethylamino)butyric acid hydrochloride was used as the starting material, to obtain Compound 5.

$^1$H-NMR (600 MHz, DMSO-d$_6$, $\delta_{ppm}$): 13.57 (s, 1H), 10.81 (s, 1H), 9.09 (s, 1H), 7.70 (m, 1H), 7.65 (s, 1H), 6.90 (m, 1H), 6.85 (m, 1H), 2.30 (t, 2H), 2.25 (t, 2H), 2.20 (s, 3H), 2.17 (s, 3H), 1.72 (m, 2H), 2.14 (s, 6H).

ESI-MS: [M+H]$^+$ 385, [M−H]$^−$ 383.

Example 6

Synthesis of N-{5-[5-fluoro-2-oxo-1,2-dihydro-indol-(3Z)-ylidenemethyl]-2,4-dimethyl-1H-pyrrol-3-yl}-3-(N,N-dimethylamino)propionamide

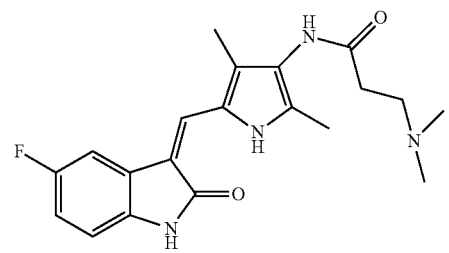

Compound 6

The reaction steps are similar to the steps described in Example 1, in which 4-(N,N-dimethylamino)propionic acid hydrochloride was used as the starting material, to obtain Compound 6.

$^1$H-NMR (600 MHz, DMSO-d$_6$, $\delta_{ppm}$): 13.59 (s, 1H), 10.86 (s, 1H), 9.50 (s, 1H), 8.80 (s, 1H), 7.70 (m, 1H), 7.66 (s, 1H), 6.90 (m, 1H), 6.85 (m, 1H), 3.16 (t, 2H), 2.77 (t, 2H), 2.20 (s, 3H), 2.18 (s, 3H), 2.63 (s, 6H).

ESI-MS: [M+H]$^+$ 371, [M−H]$^−$ 369.

Example 7

Synthesis of N-{5-[5-fluoro-2-oxo-1,2-dihydro-indol-(3Z)-ylidenemethyl]-2,4-dimethyl-1H-pyrrol-3-yl}-acrylamide

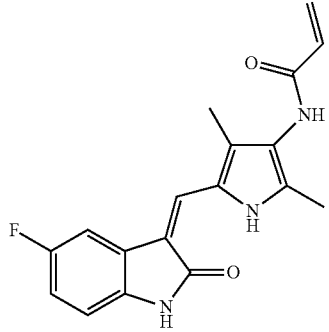

Compound 7

The reaction steps are similar to the steps described in Example 1, in which acryloyl chloride was used as the reagent in the last step, to obtain Compound 7 directly.

ESI-MS: [M+H]$^+$ 326, [M−H]$^−$ 324.

Example 8

Synthesis of N-{5-[5-methylsulfonylamino-2-oxo-1,2-dihydro-indol-(3Z)-ylidenemethyl]-2,4-dimethyl-1H-pyrrol-3-yl}-3-(N,N-diethylamino)propionamide Compound 8

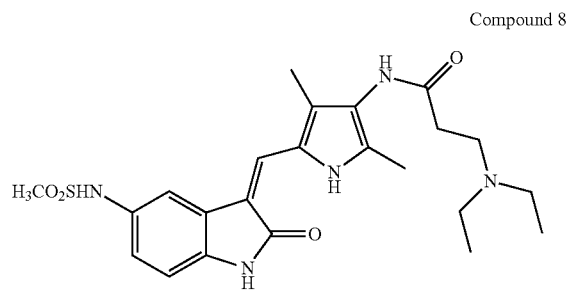

The reaction steps are similar to the steps described in Example 1, in which 5-methylsulfonylamino-indol-2-one was used as the starting material, to obtain Compound 8.
ESI-MS: [M+H]$^+$ 474, [M–H]$^-$ 472.

Example 9

Synthesis of N-{5-[5-fluoro-2-oxo-1,2-dihydro-indol-(3Z)-ylidenemethyl]-2,4-dimethyl-1H-pyrrol-3-yl}-2-(N,N-diethylamino)ethylsulfonamide Compound 9

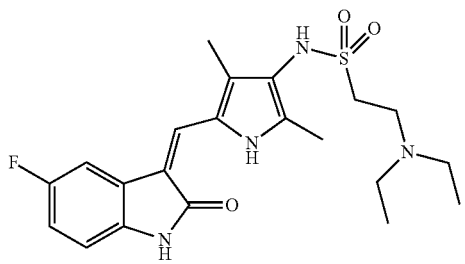

The reaction steps are similar to the steps described in Example 1, in which 2-(N,N-diethylamino)ethylsulfonyl chloride was used as the reagent in the last step, to obtain Compound 9 directly.
ESI-MS: [M+H]$^+$ 435, [M–H]$^-$ 433.

Example 10

Synthesis of N-{5-[5-fluoro-2-oxo-1,2-dihydro-indol-(3Z)-ylidenemethyl]-2,4-dimethyl-1H-pyrrol-3-yl}-3-(4-ethylpiperazin-1-yl)propionamide Compound 10

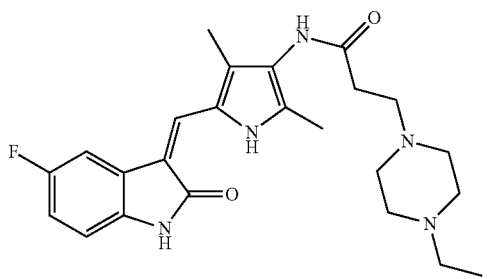

a. Synthesis of N-{5-[5-fluoro-2-oxo-1,2-dihydro-indol-(3Z)-ylidenemethyl]-2,4-dimethyl-1H-pyrrol-3-yl}-3-bromo-propionamide

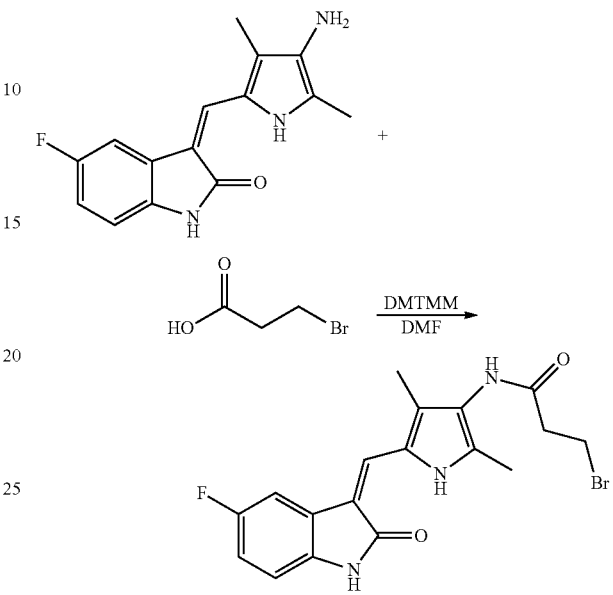

3-bromopropionic acid (338 mg, 1.2 eq) was dissolved in 5 ml of DMF and stirred at room temperature to obtain a solution. To the reaction solution was added DMTMM (618 mg, 1.2 eq). The mixture was stirred at room temperature for 20 min, followed by the addition of (3Z)-[(3,5-dimethyl-4-amino-1-hydropyrrol-2-yl)methylene]-5-fluoro-indol-2-one (501 mg, 1.0 eq). The mixture was stirred and reacted at room temperature for 2 h. Once the reaction was completed as indicated by TLC, the reaction solution was added to 200 ml of ethyl acetate. Solid product was formed, collected by filtration, washed with ethyl acetate and dried, to obtain the target product, 548 mg (yield 73%).

b. Synthesis of N-{5-[5-fluoro-2-oxo-1,2-dihydro-indol-(3Z)-ylidenemethyl]-2,4-dimethyl-1H-pyrrol-3-yl}-3-(4-ethylpiperazin-1-yl)propionamide

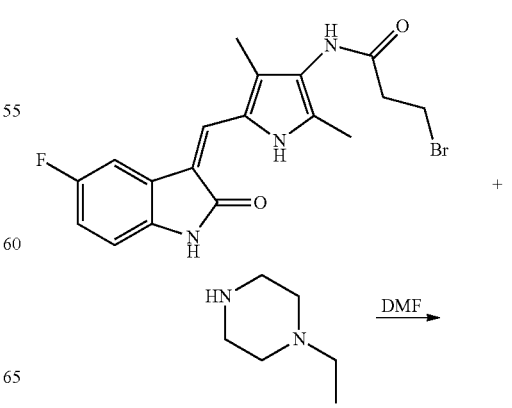

-continued

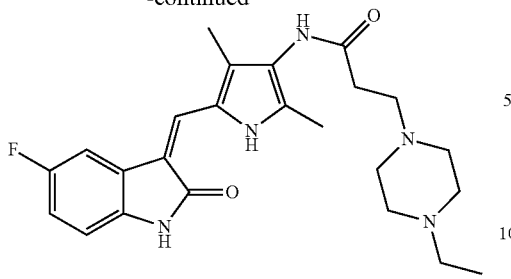

N-{5-[5-fluoro-2-oxo-1,2-dihydro-indol-(3Z)-ylidenemethyl]-2,4-dimethyl-1H-pyrrol-3-yl}-3-bromo-propionamide (548 mg, 1.0 eq) was dissolved in 4 ml of DMF, stirred at room temperature to obtain a solution. To the solution was added 4-ethylpiperazine (850 mg, 4.0 eq). The reaction mixture was heated to 50° C. and reacted for 4 h. Once the reaction was completed as indicated by TLC, the reaction solution was added to 200 ml of ethyl acetate. Solid product was formed, collected by filtration, washed with ethyl acetate, dried, and purified by column chromatograph to obtain the target compound of 312 mg (yield 32%).

$^1$H-NMR (600 MHz, DMSO-d$_6$, δ$_{ppm}$): 13.57 (s, 1H), 10.81 (s, 1H), 9.20 (s, 1H), 7.69 (d, 1H, J=9.0), 7.65 (s, 1H), 6.85 (m, 1H), 6.84 (m, 1H), 2.61 (t, 2H), 2.43 (t, 4H), 2.29 (m, 6H), 2.20 (s, 3H), 2.17 (s, 3H), 0.98 (t, 3H).

ESI-MS: [M+H]$^+$ 440, [M–H]$^-$ 438.

Example 11

Synthesis of N-{5-[5-fluoro-2-oxo-1,2-dihydro-indol-(3Z)-ylidenemethyl]-2,4-dimethyl-1H-pyrrol-3-yl}-3-(4-methylpiperazin-1-yl)propionamide Compound 11

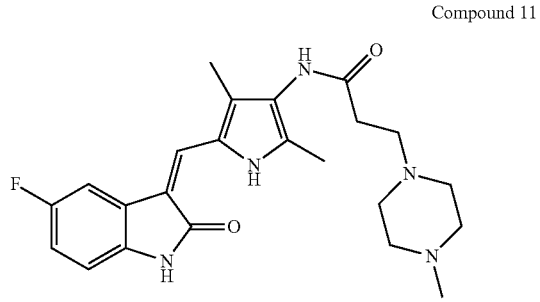 [SMILES: Cc1[nH]c(/C=C2\C(=O)Nc3ccc(F)cc32)c(C)c1NC(=O)CCN1CCN(C)CC1]

The reaction steps of Example 10 were repeated, in which 4-methylpiperazine was used as the reagent in the last step, to obtain Compound 11.

$^1$H-NMR (600 MHz, DMSO-d$_6$, δ$_{ppm}$): 13.57 (s, 1H), 10.81 (s, 1H), 9.20 (s, 1H), 7.69 (d, 1H, J=9.0), 7.66 (s, 1H), 6.88 (m, 1H), 6.83 (m, 1H), 2.61 (t, 2H), 2.42 (t, 4H), 2.20 (s, 3H), 2.17 (s, 3H), 2.15 (t, 3H).

ESI-MS: [M+H]$^+$ 426, [M–H]$^-$ 424.

Example 12

Syntheis of N-{5-[5-fluoro-2-oxo-1,2-dihydro-indol-(3Z)-ylidenemethyl]-2,4-dimethyl-1H-pyrrol-3-yl}-3-(morpholin-4-yl)propionamide Compound 12

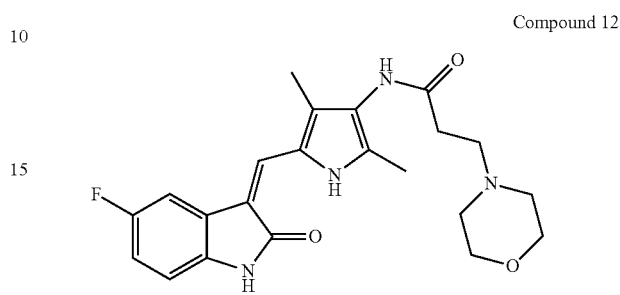

The reaction steps of Example 10 were repeated, in which morpholine was used as the reagent in the last step, to obtain Compound 12.

$^1$H-NMR (600 MHz, DMSO-d$_6$, δ$_{ppm}$): 13.57 (s, 1H), 10.81 (s, 1H), 9.19 (s, 1H), 8.74 (broad s, 1H), 7.69 (m, 1H), 7.65 (s, 1H), 6.89 (m, 1H), 6.83 (m, 2H), 3.76 (m, 6H), 3.59 (m, 3H), 3.09 (m, 8H) 2.45 (m, 4H), 2.20 (s, 3H), 2.17 (s, 3H).

ESI-MS: [M+H]$^+$ 413, [M–H]$^-$ 411.

Compound 12 was dissolved in methanol to form a solution, and the solution was slowly added dropwise to a L-malic acid solution in acetonitrile. The reaction mixture was refluxed for 2 h. An orange yellow solid was formed, collected by filtration, washed with acetonitrile for a few times, and dried to obtain the L-malate salt of Compound 12.

Example 13

Synthesis of N-{5-[5-fluoro-2-oxo-1,2-dihydro-indol-(3Z)-ylidenemethyl]-2,4-dimethyl-1H-pyrrol-3-yl}-3-(piperidin-1-yl)propionamide Compound 13

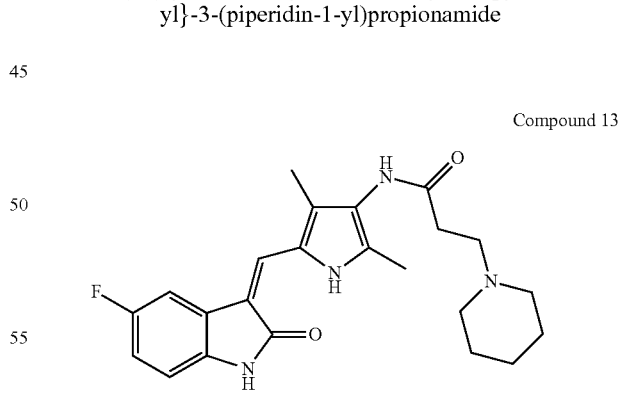

The reaction steps of Example 10 were repeated, in which piperidine was used as the reagent in the last step, to obtain Compound 13.

$^1$H-NMR (600 MHz, DMSO-d$_6$, δ$_{ppm}$): 13.58 (s, 1H), 10.83 (s, 1H), 9.19 (s, 1H), 7.70 (m, 1H), 7.66 (s, 1H), 6.89 (m, 1H), 6.83 (m, 2H), 3.00 (m, 8H), 2.45 (m, 4H), 2.20 (s, 3H), 2.17 (s, 3H). 1.18 (m, 6H).

ESI-MS: [M+H]$^+$ 411, [M–H]$^-$ 409.

Example 14

Synthesis of N-{5-[5-fluoro-2-oxo-1,2-dihydro-indol-(3Z)-ylidenemethyl]-2,4-dimethyl-1H-pyrrol-3-yl}-3-(tetrahydropyrrol-1-yl)propionamide Compound 14

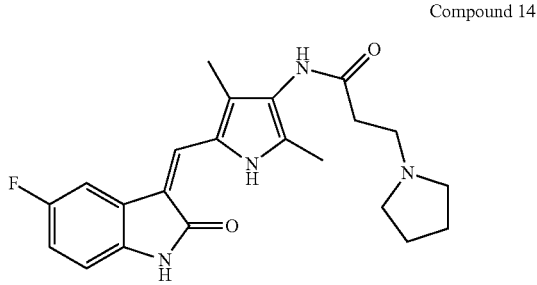 [SMILES: Cc1[nH]c(/C=C2\C(=O)Nc3ccc(F)cc32)c(C)c1NC(=O)CCN1CCCC1]

The reaction steps of Example 10 were repeated, in which tetrahydropyrrole was used as the reagent in the last step, to obtain Compound 14 (yield 63.4%).

¹H-NMR (600 MHz, DMSO-d₆, δ$_{ppm}$): 13.57 (s, 1H), 10.80 (s, 1H), 9.25 (s, 1H), 7.69 (d, 1H, J=9.0), 7.65 (s, 1H), 6.89 (m, 1H), 6.83 (m, 1H), 2.71 (t, 2H), 2.49 (m, 4H), 2.44 (t, 2H), 2.19 (s, 3H), 2.16 (s, 3H), 1.67 (m, 4H).

ESI-MS: [M+H]⁺ 397.3, [M−H]⁻ 395.2.

Example 15

Synthesis of N-{5-[5-fluoro-2-oxo-1,2-dihydro-indol-(3Z)-ylidenemethyl]-2,4-dimethyl-1H-pyrrol-3-yl}-2-(4-methylpiperazin-1-yl)acetamide Compound 15

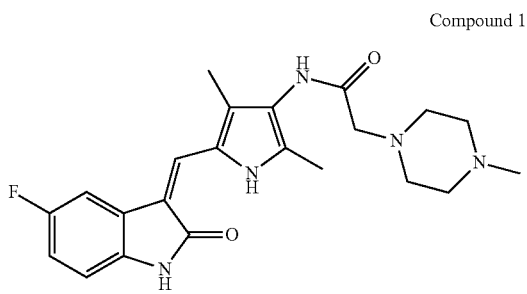

a. Synthesis of 2-chloro-N-{5-[5-fluoro-2-oxo-1,2-dihydro-indol-(3Z)-ylidenemethyl]-2,4-dimethyl-1H-pyrrol-3-yl}acetamide

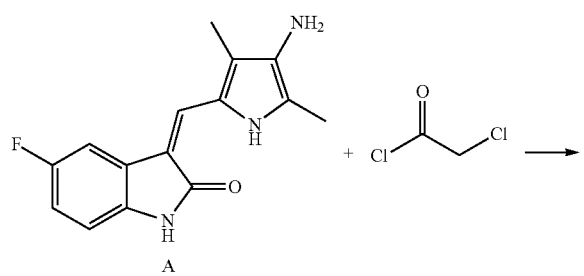

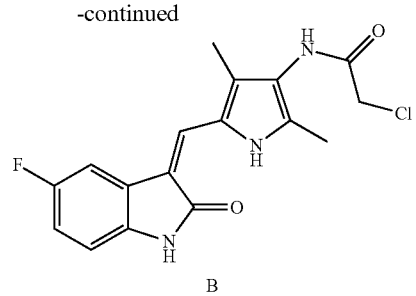

B

Intermediate A (30 g) was mixed with THF (3 L) to obtain a solution by stirring. To the solution was added 16.8 ml of triethylamine. The mixture was cooled to 5° C. or below, to which was added dropwise a solution of chloroacetyl chloride (15 g) in THF (15 ml). A yellow solid was formed. The reaction temperature was maintained at 0° C. or below and the reaction was allowed to continue for another 20 min. Once the intermediate A disappeared as indicated by TLC, the reaction mixture was filtered and the filter cake was washed with THF (200 ml) and DCM(100 ml), respectively, and then pulped with 3 L of water and 100 ml of acetone. The resultant mixture was allowed to stand at room temperature to reach a constant weight, to obtain the target product 36.2 g (yield 93.8%).

b. Synthesis of N-{5-[5-fluoro-2-oxo-1,2-dihydro-indol-(3Z)-ylidenemethyl]-2,4-dimethyl-1H-pyrrol-3-yl}-2-(4-methylpiperazin-1-yl)acetamide

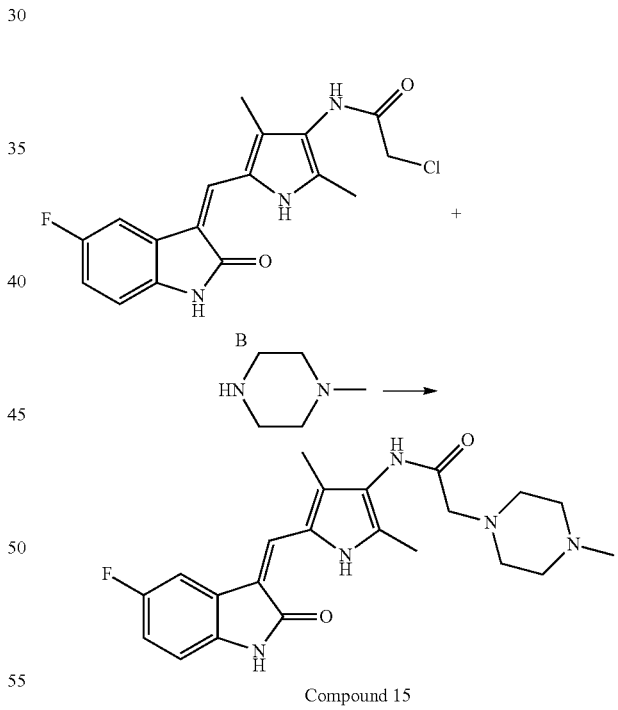

Compound 15

Intermediate B (8 g) was mixed with DMF (40 ml) to abtain a solution by stirring at room temperature. To the solution was added N-methylpiperazine. The mixture was heated to 55° C. and reacted for 4 h. Once the intermediate B was consumed completely as indicated by TLC, the reaction mixture was cooled to room temperature on its own accord, to which was added ethyl acetate (200 ml). The mixture was stirred, solid product was collected by filtration, and washed with a mixture of ethyl acetate/DMF (5:1), to obtain the target product (yield 50.3%).

¹H-NMR (600 MHz, DMSO-d$_6$, δ$_{ppm}$): 13.61 (s, 1H), 10.85 (s, 1H), 9.20 (s, 1H), 7.72 (dd, 1H, J$_1$=2.4, J$_2$=9.0), 7.68 (s, 1H), 6.91 (m, 1H), 6.84 (m, 1H), 3.37 (m, 2H), 3.26 (s, 2H), 3.11-3.04 (m, 4H), 2.68 (m, 2H), 2.75 (s, 3H), 2.22 (s, 3H), 2.19 (s, 3H).

ESI-MS: [M+H]$^+$ 412.1, [M−H]$^−$ 410.2.

Example 16

Synthesis of N-{5-[5-fluoro-2-oxo-1,2-dihydro-indol-(3Z)-ylidenemethyl]-2,4-dimethyl-1H-pyrrol-3-yl}-2-(piperidin-1-yl)acetamide Compound 16

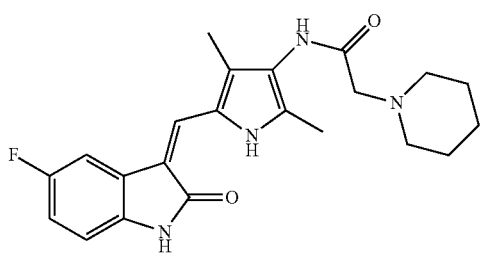

The reaction steps are similar to the steps described in Example 15, in which piperidine was used as the reagent in the last step, to obtain Compound 16 (yield 66.1%).

¹H-NMR (600 MHz, DMSO-d$_6$, δ$_{ppm}$): 13.64 (s, 1H), 10.90 (s, 1H), 10.16 (s, 1H), 7.96 (s, 1H), 7.72 (dd, 1H, J$_1$=2.4, J$_2$=9.0), 7.68 (s, 1H), 6.92 (m, 1H), 6.84 (m, 1H), 3.46 (s, 2H), 3.02 (m, 4H), 2.24 (s, 3H), 2.20 (s, 3H), 1.66 (m, 4H), 2.54 (m, 4H).

ESI-MS: [M+H]$^+$ 397.3, [M−H]$^−$ 395.2.

Example 17

Synthesis of N-{5-[5-fluoro-2-oxo-1,2-dihydro-indol-(3Z)-ylidenemethyl]-2,4-dimethyl-1H-pyrrol-3-yl}-2-(tetrahydropyrrol-1-yl)acetamide Compound 17

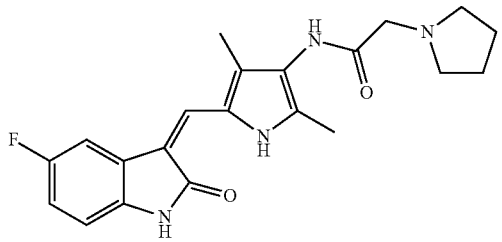

The reaction steps are similar to the steps described in Example 15, in which tetrahydropyrrole was used as the reagent in the last step, to obtain Compound 17 (yield 58.9%).

ESI-MS: [M+H]$^+$ 383.2, [2M+H]$^+$ 765.3, [M−H]$^−$ 381.3.

Example 18

Synthesis of N-{5-[5-fluoro-2-oxo-1,2-dihydro-indol-(3Z)-ylidenemethyl]-2,4-dimethyl-1H-pyrrol-3-yl}-2-(4-ethylpiperazin-1-yl)acetamide Compound 18

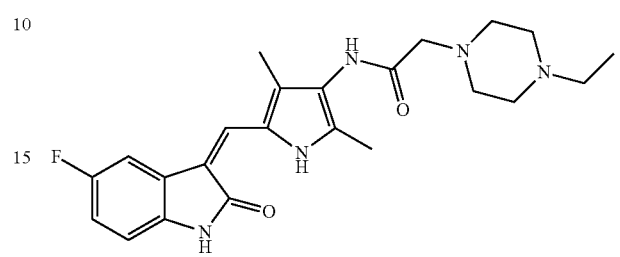

The reaction steps are similar to the steps described in Example 15, in which N-ethylpiperazine was used as the reagent in the last step, to obtain Compound 18 (yield 61.2%).

ESI-MS: [M+H]$^+$ 426.1, [M−H]$^−$ 424.2.

Example 19

Synthesis of N-{5-[5-fluoro-2-oxo-1,2-dihydro-indol-(3Z)-ylidenemethyl]-2,4-dimethyl-1H-pyrrol-3-yl}-2-(morpholin-4-yl)acetamide Compound 19

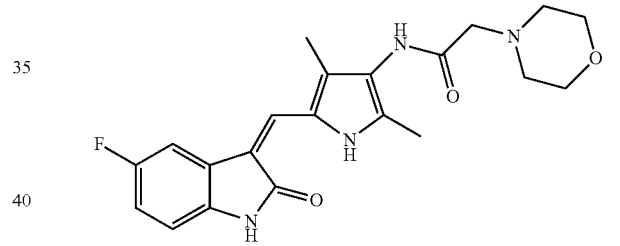

The reaction steps are similar to the steps described in Example 15, in which morpholine was used as the reagent in the last step, to obtain Compound 19 (yield 47.7%).

ESI-MS: [M+H]$^+$ 399.5, [2M+H]$^+$ 797.3.

Example 20

Synthesis of N-{5-[5-fluoro-2-oxo-1,2-dihydro-indol-(3Z)-ylidenemethyl]-2,4-dimethyl-1H-pyrrol-3-yl}-2-(N,N-diethylamino)acetamide Compound 20

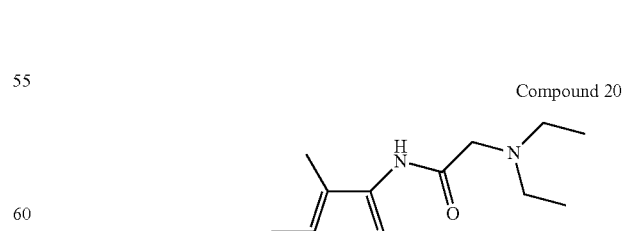

The reaction steps are similar to the steps described in Example 15, in which diethylamine was used as the reagent in the last step, to obtain Compound 20 (yield 40.8%).
ESI-MS: [M+H]⁺ 385.2, [2M+H]⁺ 769.3, [M−H]⁻ 383.1.

Example 21

Synthesis of N-{5-[5-chloro-2-oxo-1,2-dihydro-indol-(3Z)-ylidenemethyl]-2,4-dimethyl-1H-pyrrol-3-yl}-2-(N,N-diethylamino)acetamide

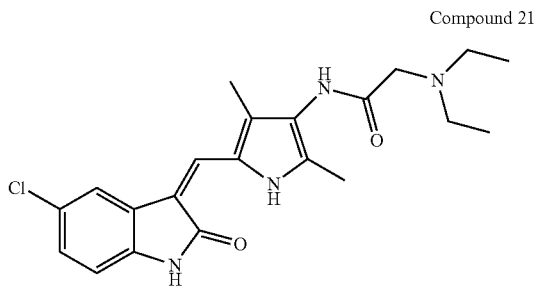 [SMILES: CCN(CC)CC(=O)Nc1c(C)[nH]c(/C=C2\C(=O)Nc3ccc(Cl)cc32)c1C]

Compound 21

The reaction steps are similar to the steps described in Example 15, in which (3Z)-[(3,5-dimethyl-4-amino-1-hydropyrrol-2-yl)methylene]-5-chloro-indol-2-one was used as the starting material, and diethylamine was used as the reagent in the last step, to obtain Compound 21 (yield 33.5%).
ESI-MS: [M+H]⁺ 401.1, [M−H]⁻ 399.2.

Example 22

Synthesis of N-{5-[5-fluoro-2-oxo-1,2-dihydro-indol-(3Z)-ylidenemethyl]-2,4-dimethyl-1H-pyrrol-3-yl}-2-(N,N-dimethylamino)acetamide

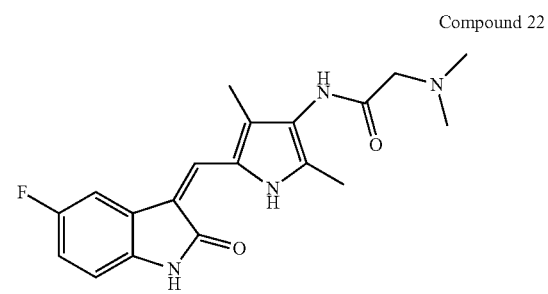 [SMILES: Cc1[nH]c(/C=C2\C(=O)Nc3ccc(F)cc32)c(C)c1NC(=O)CN(C)C]

Compound 22

The reaction steps are similar to the steps described in Example 15, in which dimethylamine was used as the reagent in the last step, to obtain Compound 22 (yield 33.1%).
ESI-MS: [M+H]⁺ 355.2, [M−H]⁻ 353.1.
Similarly, we further obtained the following compounds:

| No. | Name | Structure | ESI-MS |
|---|---|---|---|
| Comp. 23 | N-{5-[6-methoxy-2-oxo-1,2-dihydro-indol-(3Z)-ylidenemethyl]-2,4-dimethyl-1H-pyrrol-3-yl}-2-(N,N-diethylamino)acetamide | 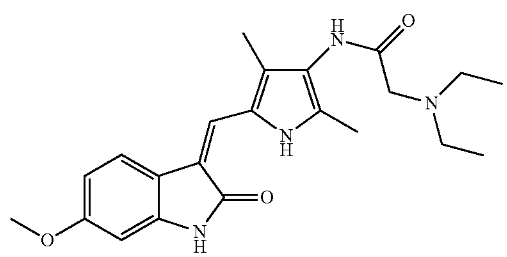 [SMILES: CCN(CC)CC(=O)Nc1c(C)[nH]c(/C=C2\C(=O)Nc3cc(OC)ccc32)c1C] | [M + H]⁺ 397.2, [M − H]⁻ 395.3 |
| Comp. 24 | N-{5-[6-trifluoromethyl-2-oxo-1,2-dihydro-indol-(3Z)-ylidenemethyl]-2,4-dimethyl-1H-pyrrol-3-yl}-2-(N,N-diethylamino)acetamide | 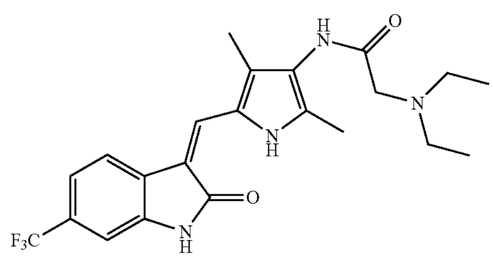 [SMILES: CCN(CC)CC(=O)Nc1c(C)[nH]c(/C=C2\C(=O)Nc3cc(C(F)(F)F)ccc32)c1C] | [M + H]⁺ 435.1, [M − H]⁻ 433.2 |
| Comp. 25 | N-{5-[5-methylsulfonylamino-2-oxo-1,2-dihydro-indol-(3Z)-ylidenemethyl]-2,4-dimethyl-1H-pyrrol-3-yl}-2-(N,N-diethylamino)acetamide | 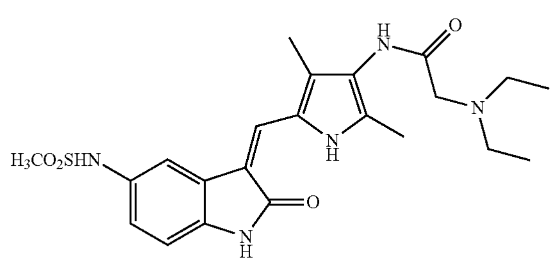 | [M + H]⁺ 458.3, [M − H]⁻ 456.1 |

-continued

| No. | Name | Structure | ESI-MS |
|---|---|---|---|
| Comp. 26 | N-{5-[5-nitro-2-oxo-1,2-dihydro-indol-(3Z)-ylidenemethyl]-2,4-dimethyl-1H-pyrrol-3-yl}-2-(N,N-diethylamino)acetamide | 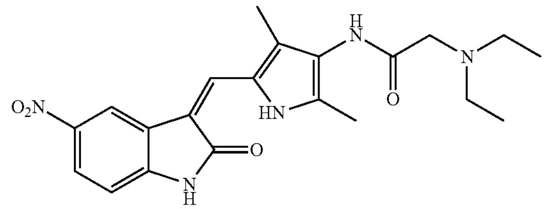 | [M + H]+ 371.3, [M − H]− 369.2 |
| Comp. 27 | N-{5-[6-methyl-2-oxo-1,2-dihydro-indol-(3Z)-ylidenemethyl]-2,4-dimethyl-1H-pyrrol-3-yl}-2-(N,N-diethylamino)acetamide | 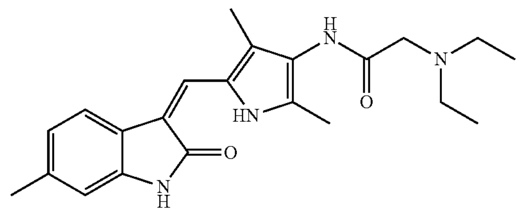 [SMILES: CCN(CC)CC(=O)Nc1c(C)[nH]c(/C=C2\C(=O)Nc3cc(C)ccc32)c1C] | [M + H]+ 327.1, [M − H]− 325.1 |
| Comp. 28 | N-{5-[5-acetylamino-2-oxo-1,2-dihydro-indol-(3Z)-ylidenemethyl]-2,4-dimethyl-1H-pyrrol-3-yl}-2-(N,N-diethylamino)acetamide | 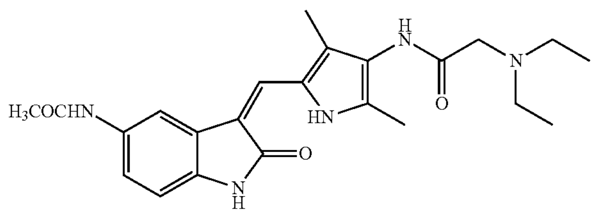 | [M + H]+ 387.5, [M − H]− 385.3 |

Biological Experiments

As for the compounds of the present invention, their inhibitory actions on angiogenesis in vitro, their toxicity to the selected tumor cell strains (all tumor cell strains were purchased from the Institute of Biochemistry and Cell Biology, SIBS, CAS) and their inhibitory actions on nude mice transplanted tumor in vivo were determined by the following experiments.

A) Inhibitory Actions on Arterial Ring Angiogenesis in Rats

This experiment was conducted by referring to the method described by R. F. Nicosia et al (Nicosia, R. F., et al. Am J Pathol., 1997, 151, 1379-1386).

Rats were executed by cervical dislocation. The thoracic aorta was carefully separated, and placed in a container with physiological saline. The excess tissues were carefully cut off. The blood vessels were cut with a pair of ophthalmic scissors to form 1 mm thick vascular ring slices. To a pre-cooled 96-well cell culture plate, one separated vascular ring was placed in the center of each well. 70 μl of pre-molten Matrigel was carefully added to cover the vascular ring, which was incubated at 37° C. for 1 h so as to solidify it. The compound to be tested was diluted with RPMI1640 culture medium containing 10% FBS to have a concentration twice of the final concentration, and 70 μl of which was added to each well. The sample was placed in incubator for conventional culture, and each compound was tested at least in two repeated wells, and each test was repeated twice. Positive control Sunitinib and the compounds of the present invention were set to have gradient concentrations of 5, 1, 0.2 μg/ml, and negative control wells were set not containing the compounds of the present invention. The fresh culture medium was replaced every 3 days, and the drug was changed at the same time. The survival status of vascular rings was observed under microscope, and pictures were taken at the same time. Image Pro Plus software was used to calculate the area covered by micrangiums. The average inhibition rate was calculated by using the formula: inhibition rate (%)=(area of control well−area of drug well)/area of control well×100%. The results are shown in Table 1.

TABLE 1

Analysis of inhibitory actions of the compounds of the present invention on arterial ring angiogenesis in rats

| Tested substance | Inhibitory rate (%) | | |
|---|---|---|---|
| | 5 μg/ml | 1 μg/ml | 0.2 μg/ml |
| Sunitinib | 100 | 100 | 95 |
| Compound 1 | 100 | 100 | 99 |
| Compound 2 | 100 | 100 | 94 |
| Compound 3 | 100 | 100 | 93 |
| Compound 4 | 100 | 100 | 98 |
| Compound 5 | 100 | 100 | 93 |
| Compound 6 | 100 | 100 | 92 |
| Compound 7 | 100 | 100 | 95 |
| Compound 8 | 100 | 100 | 94 |
| Compound 9 | 100 | 100 | 93 |
| Compound 10 | 100 | 100 | 98 |
| Compound 11 | 100 | 100 | 99 |
| Compound 12 | 100 | 100 | 94 |
| Compound 13 | 100 | 100 | 93 |
| Compound 14 | 100 | 100 | 88 |
| Compound 15 | 100 | 100 | 89 |
| Compound 16 | 100 | 100 | 91 |
| Compound 17 | 100 | 100 | 89 |
| Compound 18 | 100 | 100 | 99 |
| Compound 19 | 100 | 100 | 89 |
| Compound 20 | 100 | 100 | 98 |
| Compound 21 | 100 | 100 | 95 |
| Compound 22 | 100 | 100 | 90 |
| Compound 23 | 100 | 100 | 90 |
| Compound 24 | 100 | 100 | 98 |
| Compound 25 | 100 | 100 | 89 |
| Compound 26 | 100 | 100 | 93 |

TABLE 1-continued

Analysis of inhibitory actions of the compounds of the present invention on arterial ring angiogenesis in rats

| Tested substance | Inhibitory rate (%) | | |
|---|---|---|---|
| | 5 μg/ml | 1 μg/ml | 0.2 μg/ml |
| Compound 27 | 100 | 95 | 78 |
| Compound 28 | 100 | 100 | 90 |

B) Cytotoxicity Test

Cytotoxicity of the compounds of the present invention was tested with human non-small cell lung cancer cells A549, human cervical cancer Hela cells, human skin cancer cells A431. The test was performed by referring to the method described by Rusnak et al (Rusnak D. W., et al., Cell Prolif., 2007, 40, 580-94).

In Dulbecco's Modified Eagle Medium (DMEM) comprising 10% fetal bovine serum, 2 mM glutamine and non-essential amino acids, cells were cultured at 37° C. in 5% $CO_2$ cell incubator. Trypsin/ethylenediamine tetraacetic acid (EDTA) were used to harvest cells in cell culture bottle. The cells were added to a 96-well cell culture plate, 4000/well (0.1 ml medium), adhering wall overnight, 0.1 ml of the diluted solution of the compounds to be tested was added, the final concentration of DMSO was 0.25%. The cell culture plate was incubated at 37° C., 5% $CO_2$ conditions for 72 h. The change of cellular morphology was observed under microscope, and then 50 μl of 50% (mass/volume) trichloroacetic acid (TCA) was added to each well to fix cells. The final concentration of TCA was 10%. It stood for 5 min, than was placed in 4° C. refrigerator for 1 h, the wells of the culture plate were washed with deionized water for 5 times to remove TCA, drained, dried in air until no wet trace was observed. 100 μl of 0.4% (mass/volume) SRB was added to each well, stood at room temperature for 10 min. The liquid in each well was discarded, and then the wells were washed with 1% acetic acid for 5 times, dried in air, extracted with 150 μl of 10 mM Tris base (trihydroxymethylaminomethane, pH 10.5). The absorption at a wavelength of 540 nm was measured. The $IC_{50}$ (μM) of the compound was calculated using Logit method. The results are given in Table 2.

TABLE 2

Analysis of toxicity of the compounds of the present invention on three kinds of tumor cells

| Substance to be tested | Cytotoxicity test $IC_{50}$(μM) | | |
|---|---|---|---|
| | A549 | Hela | A431 |
| Sunitinib | 11.52 | 2.027 | 1.931 |
| Compound 1 | >30 | >30 | >30 |
| Compound 2 | >30 | >30 | >30 |
| Compound 3 | >30 | 5.084 | >30 |
| Compound 4 | >30 | >30 | >30 |
| Compound 5 | >30 | >30 | >30 |
| Compound 6 | >30 | 8.084 | >30 |
| Compound 7 | >30 | 6.782 | >30 |
| Compound 8 | >30 | >30 | >30 |
| Compound 9 | >30 | >30 | 8.579 |
| Compound 10 | >30 | >30 | >30 |
| Compound 11 | >30 | >30 | >30 |
| Compound 12 | >30 | 4.753 | 7.595 |
| Compound 13 | >30 | >30 | 8.688 |
| Compound 14 | >30 | >30 | >30 |
| Compound 15 | >30 | >30 | >30 |
| Compound 16 | >30 | >30 | 6.254 |
| Compound 17 | >30 | >30 | >30 |
| Compound 18 | >30 | 4.153 | >30 |
| Compound 19 | >30 | >30 | 7.601 |
| Compound 20 | >30 | 5.210 | >30 |
| Compound 21 | >30 | >30 | >30 |
| Compound 22 | >30 | >30 | >30 |
| Compound 23 | >30 | >30 | >30 |
| Compound 24 | >30 | 3.557 | 8.891 |
| Compound 25 | >30 | >30 | 6.565 |
| Compound 26 | >30 | 4.618 | >30 |
| Compound 27 | >30 | >30 | >30 |
| Compound 28 | >30 | >30 | >30 |

The results of rat arterial ring test and cytotoxicity test show that the compounds of the present invention have better inhibitory activity on angiogenesis in vitro, and have relative low cytotoxicity to tumor cells. In the rat arterial ring test, all of the 11 compounds at a concentration of 0.2 μg/m$^1$ can almost completely inhibit the generation of micrangiums, and their activity are better than or close to the positive control Sunitinib. In the cytotoxicity test, except that Compound 3, Compound 6, Compound 7 and Compound 9, Compound 12, Compound 13, Compound 19 and Compound 20 have certain toxicity to some cells, all other compounds have less cytotoxicity than the positive control Sunitinib. The results show that the compounds of the present invention can effectively inhibit angiogenesis, and have relatively low cytotoxicity, exhibiting potential anti-tumor effects on human tumor growth by inhibiting tumor angiogenesis.

C) Nude Mice Transplanted Tumor Test

The nude mice transplanted tumor test used female Balb/cA nude mice, and tumor strains were human colon cancer HT 29 strains.

Under sterile condition, eugonic tumor tissues stage were cut into pieces of about 1.5 mm$^3$, and inoculated at right axillary fossa of the nude mice. The transplanted tumor diameter was measured by vernier caliper, and the animals were randomly grouped after the tumors grew to about 120 mm$^3$. The positive control group and the compounds group in a dosage of 80 mg/kg were administered intragastrically each day for consecutive 20 days. The negative control group was given equivalent amount of injection water containing 0.1% Tween 80. Tumor diameters and the bodyweight of mice were measured 2-3 times every week. The evaluation indexes observed in the test include relative tumor proliferation rate, bodyweight and general states. The formulation for calculating tumor volume (TV) is: TV=½×a×b$^2$, wherein a, b represent major diameter and minor diameter of tumor; Relative tumor volume (RTV) was calculated according the results of measurement by the following formula: RTV=$V_t/V_0$, wherein $V_0$ is tumor volume measured when dividing groups for administration, and $V_t$ is tumor volume measured after each administration.

The index for evaluating anti-tumor activity is relative tumor proliferation rate T/C (%), the formulation for calculation thereof is: T/C(%)=($T_{RTV}/C_{RTV}$)×100%, wherein $T_{RTV}$ is RTV of the therapeutic group; $C_{RTV}$ is the RTV of the negative control group.

Relative tumor growth inhibition rate=(1−T/C)×100%

Evaluation standard: "ineffective" is given when the relative tumor growth inhibition rate <40%, and "effective" is given when the relative tumor growth inhibition rate ≥40% and statistic treatment shows P<0.05. The test results are shown in Table 3.

TABLE 3

Analysis of the therapeutic effects of the compounds of the present invention on human colon cancer HT 29 transplanted tumor in nude mice

| Test substance | $d_0$ | | $d_{21}$ | | | Tumor inhibition rate $d_{21}$ (%) | Dead animal number |
|---|---|---|---|---|---|---|---|
| | $V_{ave} \pm SD$ | $W_{ave} \pm SD$ | $V_{ave} \pm SD$ | $RTV \pm SD$ | $W_{ave} \pm SD$ | | |
| Negative control | 113.6 ± 34.5 | 18.9 ± 1.35 | 811.3 ± 236.8 | 7.19 ± 0.92 | 19.6 ± 2.98 | 0 | 0/6 |
| Sunitinib | 121.6 ± 39.5 | 19.4 ± 0.44 | 129.6 ± 45.8* | 0.83 ± 0.28 | 17.3 ± 1.56 | 88.5 | 1/6 |
| Compound 1 | 118.5 ± 37.5 | 18.6 ± 1.20 | 102.8 ± 26.2* | 0.94 ± 0.12 | 18.8 ± 2.97 | 86.9 | 0/6 |
| Compound 2 | 115.4 ± 30.5 | 18.8 ± 0.35 | 300.3 ± 36.8*# | 2.60 ± 0.52 | 19.9 ± 0.68 | 63.8 | 0/6 |
| Compound 3 | 123.4 ± 39.5 | 19.3 ± 0.41 | 120.6 ± 40.2* | 0.98 ± 0.36 | 17.3 ± 0.56 | 86.4 | 0/6 |
| Compound 4 | 122.2 ± 36.2 | 19.6 ± 0.22 | 80.0 ± 33.2* | 0.65 ± 0.28 | 19.6 ± 0.85 | 91.0 | 0/6 |
| Compound 5 | 116.8 ± 37.5 | 18.9 ± 1.00 | 111.8 ± 28.2* | 0.96 ± 0.42 | 18.6 ± 0.87 | 86.6 | 0/6 |
| Compound 6 | 118.3 ± 34.3 | 18.7 ± 0.38 | 130.7 ± 37.4* | 1.10 ± 0.38 | 20.4 ± 0.49 | 84.7 | 0/6 |
| Compound 7 | 124.4 ± 40.2 | 19.4 ± 0.41 | 359.8 ± 45.4*# | 2.89 ± 1.05 | 20.9 ± 0.38 | 59.8 | 0/6 |
| Compound 8 | 122.2 ± 38.4 | 19.2 ± 0.32 | 186.0 ± 53.1* | 1.52 ± 0.56 | 17.8 ± 0.65 | 78.9 | 0/6 |
| Compound 9 | 123.4 ± 40.5 | 19.6 ± 0.25 | 328.3 ± 45.4*# | 2.66 ± 0.69 | 21.4 ± 0.38 | 63.0 | 0/6 |
| Compound 10 | 115.5 ± 38.5 | 18.7 ± 1.10 | 112.8 ± 36.4* | 0.98 ± 0.34 | 18.9 ± 0.97 | 86.4 | 0/6 |
| Compound 11 | 116.3 ± 35.3 | 18.5 ± 0.55 | 96.7 ± 35.4* | 0.83 ± 0.52 | 20.5 ± 0.49 | 88.5 | 0/6 |
| Compound 12 | 121.2 ± 35.4 | 17.2 ± 0.54 | 197.9 ± 48.1* | 1.45 ± 0.37 | 19.1 ± 0.57 | 79.8 | 0/6 |
| Compound 13 | 119.6 ± 34.7 | 19.1 ± 0.85 | 253.8 ± 56.4 | 2.08 ± 0.59 | 20.1 ± 0.88 | 71.1 | 0/6 |
| Compound 16 | 119.4 ± 36.5 | 19.5 ± 0.46 | 268.4 ± 33.8* | 2.25 ± 0.37 | 18.5 ± 0.59 | 68.7 | 0/6 |
| Compound 17 | 123.6 ± 39.5 | 18.9 ± 0.58 | 324.5 ± 39.4*# | 2.63 ± 0.53 | 19.2 ± 0.82 | 63.5 | 0/6 |
| Compound 18 | 118.5 ± 40.6 | 19.1 ± 0.48 | 86.2 ± 45.3* | 0.73 ± 0.45 | 18.9 ± 0.69 | 90.1 | 0/6 |
| Compound 20 | 122.6 ± 36.4 | 19.6 ± 0.69 | 93.5 ± 42.8* | 0.76 ± 0.32 | 20.3 ± 0.63 | 89.4 | 0/6 |
| Compound 21 | 119.2 ± 38.8 | 18.9 ± 0.47 | 94.3 ± 37.2* | 0.79 ± 0.63 | 19.3 ± 0.76 | 89.0 | 0/6 |
| Compound 22 | 121.8 ± 34.5 | 19.7 ± 0.38 | 104.6 ± 43.6* | 0.86 ± 0.54 | 20.1 ± 0.35 | 88.1 | 0/6 |
| Compound 24 | 118.3 ± 36.2 | 18.6 ± 0.36 | 298.5 ± 55.8* | 2.52 ± 0.23 | 17.9 ± 0.58 | 64.9 | 0/6 |
| Compound 26 | 120.6 ± 25.4 | 19.3 ± 0.55 | 305.6 ± 46.7*# | 2.53 ± 0.43 | 20.5 ± 0.35 | 64.8 | 0/6 |
| Compound 28 | 123.5 ± 35.7 | 18.8 ± 1.01 | 204.3 ± 52.7* | 1.65 ± 0.62 | 19.5 ± 0.86 | 77.0 | 0/6 |

Notation:
(1) RTV: relative tumor volume; $V_{ave}$: average tumor volume; $W_{ave}$: average bodyweight of nude mice;
(2) *in comparison with the control group, $P < 0.05$; #in comparison with the positive control group, $P < 0.05$ The results of the nude mice transplanted tumor test show that: the compounds of the present invention have better activity of inhibiting HT-29 transplanted tumor in vivo, such as Compound 1, Compound 4, Compound 10 and Compound 11, Compound 20, Compound 21 and so on have inhibitory activity comparable to the positive control Sunitinib, and some compounds are even better. After administration of Sunitinib the bodyweight of mice decreased significantly, and the states of mice were poor, yellowing skin and blood in excrement were observed, in which one tumor-bearing mouse died after administration for 20 days. The compounds of the present invention did not cause the loss of bodyweight after administration, and the mice exhibited good states and showed no significant toxicity, which indicates that the compounds of the present invention have relatively low toxicity.

In sum, the compounds of the present invention exhibit better biological activity both in vitro and in vivo. The anti-tumor tests in vivo show the compounds have therapeutic effects comparable to the positive control Sunitinib, and have lower toxicity than the positive control Sunitinib. The results suggest that the compounds of the present invention could be developed to promising anti-tumor drugs with high efficiency and low toxicity.

Although the mode of carrying out the invention have been described in details, those skilled in the art would understand that according to the disclosed teachings, these details could be subjected to various modifications and replacements, and all of these alternations are covered by the protection scope of the present invention. The protection scope of the present invention is determined by the attached claims and any equivalents thereof.

The invention claimed is:
1. A pyrrolyl substituted dihydroindol-2-one derivative of formula I, a pharmaceutically acceptable salt thereof, a solvate of said derivative, or a solvate of said salt,

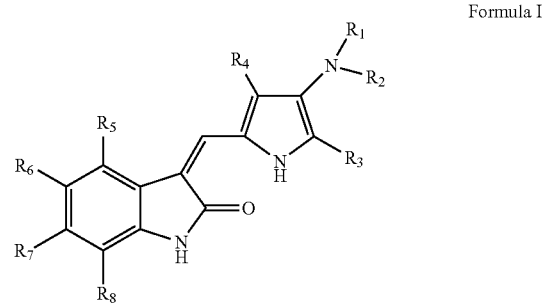

Formula I wherein,
$R_1$ is selected from the group consisting of hydrogen atom and $C_{1-4}$ alkyl;
$R_2$ is selected from the group consisting of $C_{1-4}$ alkyl, $C_{1-4}$ alkyl substituted with one or more halogen or hydroxyl groups, allyl, propargyl, —$(CH_2)_m NR_{11}R_{12}$, —$SO_j R_{11}$, —$(CH_2)_m SO_j(CH_2)_n NR_{11}R_{12}$, —$CO(CH_2)_k NR_{11}R_{12}$, —$SO_j(CH_2)_m CH$=$CH(CH_2)_n NR_{11}R_{12}$, and —$CO(CH_2)_m CH$=$CH(CH_2)_n NR_{11}R_{12}$; wherein $R_{11}$ and $R_{12}$ are each independently selected from the group consisting of hydrogen atom, $C_{1-4}$ alkyl, cycloalkyl, and heterocycloalkyl, wherein said cycloalkyl and heterocycloalkyl can be substituted with one or more substituents selected from the group consisting of halogen, alkyl, hydroxy, amino, and alkoxy groups; or $R_{11}$ and $R_{12}$ together with the N atom to which they are attached may form a 4- to 8-membered heterocycle, the heterocycle may further comprise 0 to 2 heteroatoms wherein the heteroatom is N, S, or O and the heterocycle can be substituted at any other positions, except S or O atom, with one or more substituents selected from the group consisting of $C_{1-4}$ alkyl, hydroxy-substituted $C_{1-4}$ alkyl, and —$(CH_2)_m NR_{11}R_{12}$; and wherein m, n each independently can be an integer of 0 to 4, k is an integer of 1 to 4, and j is 1 or 2;

$R_3$, $R_4$ are each independently selected from the group consisting of hydrogen atom, halogen, and $C_{1-4}$ alkyl; and $R_5$, $R_6$, $R_7$, $R_8$ are each independently selected from the group consisting of hydrogen atom, halogen, $C_{1-4}$ alkyl, $C_{1-4}$ alkyl substituted with one or more halogens, $C_{1-4}$ alkoxy, alkoxy substituted with one or more halogens, cycloalkyl, alkenyl, alkynyl, aryl, heteroaryl, hydroxy, —$NR_9R_{10}$, —$SOR_9$, —$SO_2R_9$, —$NR_9SO_2R_{10}$, —$SO_2NR_9R_{10}$, —$COR_9$, —$NR_9COR_{10}$, —$OCOR_9$, —CN, and —$NO_2$, wherein the aryl, heteroaryl, and cycloalkyl groups may be further substituted at any positions with a substituent selected from the group consisting of alkyl, halogen, haloalkyl, alkoxy, and haloalkoxy; $R_9$ and $R_{10}$ are each independently selected from the group consisting of hydrogen atom, $C_{1-4}$ alkyl, and $C_{1-4}$ alkyl substituted with one or more substituents selected from the group consisting of halogen, cycloalkyl, aryl, and heteroaryl, wherein the cycloalkyl, aryl, or heteroaryl can be substituted with one or more substituent selected from the group consisting of halogen, alkyl, hydroxy, amino, haloalkyl, alkoxy, and haloalkoxy, and wherein halogen is independently fluorine, chlorine, or bromine.

2. The pyrrolyl substituted dihydroindol-2-one derivative of formula I, a pharmaceutically acceptable salt thereof, a solvate of said derivative, or a solvate of said salt according to claim 1, wherein $R_1$ is hydrogen atom.

3. The pyrrolyl substituted dihydroindol-2-one derivative of formula I, a pharmaceutically acceptable salt thereof, a solvate of said derivative, or a solvate of said salt according to claim 1, wherein $R_5$, $R_6$, $R_7$, $R_8$ are each independently selected from the group consisting of hydrogen atom, halogen, $C_{1-4}$ alkyl, $C_{1-4}$ alkyl substituted with one or more halogens, $C_{1-4}$ alkoxy, $C_{1-4}$ alkoxy substituted with one or more halogens, alkenyl, alkynyl, hydroxy, —$NR_9R_{10}$, —$SOR_9$, —$SO_2R_9$, —$NR_9SO_2R_{10}$, —$SO_2NR_9R_{10}$, —$OCOR_9$, —CN, and —$NO_2$.

4. The pyrrolyl substituted dihydroindol-2-one derivative of formula I, a pharmaceutically acceptable salt thereof, a solvate of said derivative, or a solvate of said salt according to claim 1, wherein the pyrrolyl substituted dihydroindol-2-one derivative is selected from the group consisting of the following compounds:

N-{5-[5-fluoro-2-oxo-1,2-dihydro-indol-(3Z)-ylidenemethyl]-2,4-dimethyl-1H-pyrrol-3-yl}-3-(N,N-diethylamino)propionamide;

N-{5-[5-chloro-2-oxo-1,2-dihydro-indol-(3Z)-ylidenemethyl]-2,4-dimethyl-1H-pyrrol-3-yl}-3-(N,N-diethylamino)propionamide;

N-{5-[5-bromo-2-oxo-1,2-dihydro-indol-(3Z)-ylidenemethyl]-2,4-dimethyl-1H-pyrrol-3-yl}-3-(N,N-diethylamino)propionamide;

N-{5-[5-fluoro-2-oxo-1,2-dihydro-indol-(3Z)-ylidenemethyl]-2,4-dimethyl-1H-pyrrol-3-yl}-4-(N,N-dimethylamino)-(2E)-crotonamide;

N-{5-[5-fluoro-2-oxo-1,2-dihydro-indol-(3Z)-ylidenemethyl]-2,4-dimethyl-1H-pyrrol-3-yl}-4-(N,N-dimethylamino)butyramide;

N-{5-[5-fluoro-2-oxo-1,2-dihydro-indol-(3Z)-ylidenemethyl]-2,4-dimethyl-1H-pyrrol-3-yl}-3-(N,N-dimethylamino)propionamide;

N-{5-[5-fluoro-2-oxo-1,2-dihydro-indol-(3Z)-ylidenemethyl]-2,4-dimethyl-1H-pyrrol-3-yl}-acrylamide;

N-{5-[5-methylsulfonylamino-2-oxo-1,2-dihydro-indol-(3Z)-ylidenemethyl]-2,4-dimethyl-1H-pyrrol-3-yl}-3-(N,N-diethylamino)propionamide;

N-{5-[5-fluoro-2-oxo-1,2-dihydro-indol-(3Z)-ylidenemethyl]-2,4-dimethyl-1H-pyrrol-3-yl}-2-(N,N-diethylamino)ethylsulfonamide;

N-{5-[5-fluoro-2-oxo-1,2-dihydro-indol-(3Z)-ylidenemethyl]-2,4-dimethyl-1H-pyrrol-3-yl}-3-(4-ethylpiperazin-1-yl)propionamide;

N-{5-[5-fluoro-2-oxo-1,2-dihydro-indol-(3Z)-ylidenemethyl]-2,4-dimethyl-1H-pyrrol-3-yl}-3-(4-methylpiperazin-1-yl)propionamide;

N-{5-[5-fluoro-2-oxo-1,2-dihydro-indol-(3Z)-ylidenemethyl]-2,4-dimethyl-1H-pyrrol-3-yl}-3-(morpholin-4-yl)propionamide;

N-{5-[5-fluoro-2-oxo-1,2-dihydro-indol-(3Z)-ylidenemethyl]-2,4-dimethyl-1H-pyrrol-3-yl}-3-(piperidin-1-yl)propionamide;

N-{5-[5-fluoro-2-oxo-1,2-dihydro-indol-(3Z)-ylidenemethyl]-2,4-dimethyl-1H-pyrrol-3-yl}-3-(tetrahydropyrrol-1-yl)propionamide;

N-{5-[5-fluoro-2-oxo-1,2-dihydro-indol-(3Z)-ylidenemethyl]-2,4-dimethyl-1H-pyrrol-3-yl}-2-(4-methylpiperazin-1-yl)acetamide;

N-{5-[5-fluoro-2-oxo-1,2-dihydro-indol-(3Z)-ylidenemethyl]-2,4-dimethyl-1H-pyrrol-3-yl}-2-(piperidin-1-yl)acetamide;

N-{5-[5-fluoro-2-oxo-1,2-dihydro-indol-(3Z)-ylidenemethyl]-2,4-dimethyl-1H-pyrrol-3-yl}-2-(tetrahydropyrrol-1-yl)acetamide;

N-{5-[5-fluoro-2-oxo-1,2-dihydro-indol-(3Z)-ylidenemethyl]-2,4-dimethyl-1H-pyrrol-3-yl}-2-(4-ethylpiperazin-1-yl)acetamide;

N-{5-[5-fluoro-2-oxo-1,2-dihydro-indol-(3Z)-ylidenemethyl]-2,4-dimethyl-1H-pyrrol-3-yl}-2-(morpholin-4-yl)acetamide;

N-{5-[5-fluoro-2-oxo-1,2-dihydro-indol-(3Z)-ylidenemethyl]-2,4-dimethyl-1H-pyrrol-3-yl}-2-(N,N-diethylamino)acetamide;

N-{5-[5-chloro-2-oxo-1,2-dihydro-indol-(3Z)-ylidenemethyl]-2,4-dimethyl-1H-pyrrol-3-yl}-2-(N,N-diethylamino)acetamide;

N-{5-[5-fluoro-2-oxo-1,2-dihydro-indol-(3Z)-ylidenemethyl]-2,4-dimethyl-1H-pyrrol-3-yl}-2-(N,N-dimethylamino)acetamide;

N-{5-[6-methoxy-2-oxo-1,2-dihydro-indol-(3Z)-ylidenemethyl]-2,4-dimethyl-1H-pyrrol-3-yl}-2-(N,N-diethylamino)acetamide;

N-{5-[6-trifluoromethyl-2-oxo-1,2-dihydro-indol-(3Z)-ylidenemethyl]-2,4-dimethyl-1H-pyrrol-3-yl}-2-(N,N-diethylamino)acetamide;

N-{5-[5-methylsulfonylamino-2-oxo-1,2-dihydro-indol-(3Z)-ylidenemethyl]-2,4-dimethyl-1H-pyrrol-3-yl}-2-(N,N-diethylamino)acetamide;

N-{5-[5-nitro-2-oxo-1,2-dihydro-indol-(3Z)-ylidenemethyl]-2,4-dimethyl-1H-pyrrol-3-yl}-2-(N,N-diethylamino)acetamide;

N-{5-[6-methyl-2-oxo-1,2-dihydro-indol-(3Z)-ylidenemethyl]-2,4-dimethyl-1H-pyrrol-3-yl}-2-(N,N-diethylamino)acetamide; and N-{5-[5-acetylamino-2-oxo-1,2-dihydro-indol-(3Z)-ylidenemethyl]-2,4-dimethyl-1H-pyrrol-3-yl}-2-(N,N-diethylamino)acetamide.

5. A pharmaceutical composition, comprising the pyrrolyl substituted dihydroindol-2-one derivative of formula I, a pharmaceutically acceptable salt thereof, a solvate of said derivative, or a solvate of said salt according to claim 1, and a pharmaceutically acceptable carrier and/or excipient.

6. A method for preparing a pyrrolyl substituted dihydroindol-2-one derivative of Formula (I), wherein $R_1$ is hydrogen and $R_2$ is $-CO(CH_2)_k NR_{11}R_{12}$, comprising the following steps:

1) providing a substituted 4-nitro-2-formylpyrrole compound of Formula (II):

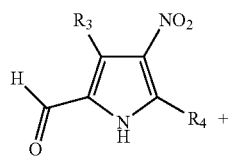

Formula (II)

2) forming compound A from the substituted 4-nitro-2-formylpyrrole compound of Formula (II) and substituted 1,3-dihydro-indol-2-one compound of Formula (III):

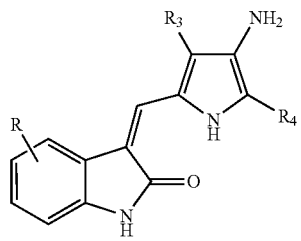

A

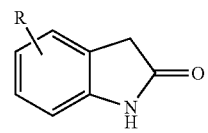

Formula (III)

3) synthesizing the compound of Formula (I) from compound A and a corresponding raw material of Formula (IV):

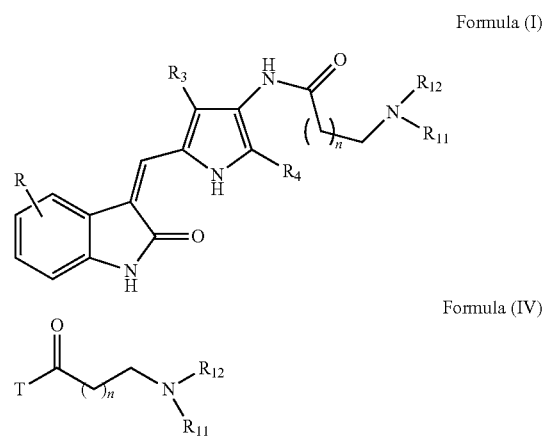

Formula (I)

Formula (IV)

wherein, k, $R_3$, $R_4$, $R_{11}$, $R_{12}$ are as defined in claim 1; R is optionally selected from one or more of $R_5$-$R_8$ as defined in claim 1; n is integer of 0 to 3, and T is selected from the group consisting of OH or Cl.

7. A method of treatment or adjunctive treatment of a tumor mediated by tyrosine kinase or tumor cell proliferation and migration driven by tyrosine kinase in a mammal comprising administering the mammal in such need an effective amount of the pyrrolyl substituted dihydroindol-2-one derivative of formula I, a pharmaceutically acceptable salt thereof, a solvate of said derivative, or a solvate of said salt according to claim 1.

8. The method according to claim 7, wherein the mammal is a human.

* * * * *